United States Patent
Kamboj et al.

Patent Number: 5,574,144
Date of Patent: Nov. 12, 1996

[54] KAINATE-BINDING, HUMAN CNS RECEPTORS OF THE EAA4 FAMILY

[75] Inventors: Rajender Kamboj, Mississauga; Candace E. Elliott; Stephen L. Nutt, both of Etobicoke, all of Canada

[73] Assignee: Allelix Biopharmaceuticals, Inc., Mississauga, Canada

[21] Appl. No.: 903,456

[22] Filed: Jun. 24, 1992

[51] Int. Cl.$^6$ .......................... C07H 21/02; C07H 21/04; C12N 5/10; C12N 15/85

[52] U.S. Cl. .................. 536/23.5; 536/24.31; 435/240.2; 435/320.1

[58] Field of Search .................. 536/26, 27, 28, 536/29, 23.1, 0.5, 24.31, 23.5; 435/240.2, 320.1

[56] References Cited

U.S. PATENT DOCUMENTS 5,202,257  4/1993  Heinemann et al. .................. 435/252.3

FOREIGN PATENT DOCUMENTS

0529995A1  8/1992  European Pat. Off. .
0529994A1  3/1993  European Pat. Off. .

WO91/06648  5/1991  WIPO .................. 530/350

OTHER PUBLICATIONS

Werner et al., Nature 351:742–744 (27 Jun. 1991).
William Sun, et al., "Molecular cloning, chromosomal mapping, and functional expression of human brain glutamate receptors"; Proc. Natl. Acad. Sci. USA, vol. 89, pp. 1443–1447, Feb. 1992.
Carmie Puckett, et al., "Molecular cloning and chromosomal localization of one of the human glutamate receptor genes"; Proc. Natl. Acad. Sci. USA, vol. 88, pp. 7557–7561, Sep. 1991.

Primary Examiner—Stephanie W. Zitomer
Attorney, Agent, or Firm—Foley & Lardner

[57] ABSTRACT

Neurotransmission by excitatory amino acids (EAAs) such as glutamate is mediated via membrane-bound surface receptors. DNA coding for one family of these receptors of the kainate-binding type of EAA receptors, has now been isolated and the receptor protein characterized. Herein described are recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

18 Claims, 13 Drawing Sheets

FIG. 1A

```
    GAATTCCCTCTCTATGACCATGCCGTGATCGTGTCTGCGGTCACCACTCGACGCATCCTC
  1 ---------+---------+---------+---------+---------+---------+  60
    CTTAAGGGAGAGATACTGGTACGGCACTAGCACAGACGCCAGTGGTGAGCTGCGTAGGAG

ATTTCTACCCGAACCCAGGAGCCGAACGCTAGATCGGGGAAGTGGGTGCCGTGCGTGTGG
 61 ---------+---------+---------+---------+---------+---------+ 120
    TAAAGATGGGCTTGGGTCCTCGGCTTGCGATCTAGCCCCTTCACCCACGGCACGCACACC

GCACAGAAACACCATGAAGATTATTTTCCCGATTCTAAGTAATCCAGTCTTCAGGCGCAC
121 ---------+---------+---------+---------+---------+---------+ 180
    CGTGTCTTTGTGGTACTTCTAATAAAAGGGCTAAGATTCATTAGGTCAGAAGTCCGCGTG

M  K  I  I  F  P  I  L  S  N  P  V  F  R  R  T  -

CGTTAAACTCCTGCTCTGTTTACTGTGGATTGGATATTCTCAAGGAACCACACATGTATT
181 ---------+---------+---------+---------+---------+---------+ 240
    GCAATTTGAGGACGAGACAAATGACACCTAACCTATAAGAGTTCCTTGGTGTGTACATAA

V  K  L  L  C  L  L  W  I  G  Y  S  Q  G  T  T  H  V  L   -
                                          |--->
                                          Mature N-terminus
    AAGATTTGGTGGTATTTTTGAATATGTGGAATCTGGCCCAATGGGAGCTGAGGAACTTGC
241 ---------+---------+---------+---------+---------+---------+ 300
    TTCTAAACCACCATAAAAACTTATACACCTTAGACCGGGTTACCCTCGACTCCTTGAACG

R  F  G  G  I  F  E  Y  V  E  S  G  P  M  G  A  E  E  L  A -

ATTCAGATTTGCTGTGAACACAATTAACAGAAACAGAACATTGCTACCCAATACTACCCT
301 ---------+---------+---------+---------+---------+---------+ 360
    TAAGTCTAAACGACACTTGTGTTAATTGTCTTTGTCTTGTAACGATGGGTTATGATGGGA

F  R  F  A  V  N  T  I  N  R  N  R  T  L  L  P  N  T  T  L -

TACCTATGATACCCAGAAGATAAACCTTTATGATAGTTTTGAAGCATCCAAGAAAGCCTG
361 ---------+---------+---------+---------+---------+---------+ 420
    ATGGATACTATGGGTCTTCTATTTGGAAATACTATCAAAACTTCGTAGGTTCTTTCGGAC

T  Y  D  T  Q  K  I  N  L  Y  D  S  F  E  A  S  K  K  A  C -

TGATCAGCTGTCTCTTGGGGTGGCTGCCATCTTCGGGCCTTCACACAGCTCATCAGCAAA
421 ---------+---------+---------+---------+---------+---------+ 480
    ACTAGTCGACAGAGAACCCCACCGACGGTAGAAGCCCGGAAGTGTGTCGAGTAGTCGTTT

D  Q  L  S  L  G  V  A  A  I  F  G  P  S  H  S  S  S  A  N -

CGCAGTGCAGTCCATCTGCAATGCTCTGGGAGTTCCCCACATACAGACCCGCTGGAAGCA
481 ---------+---------+---------+---------+---------+---------+ 540
    GCGTCACGTCAGGTAGACGTTACGAGACCCTCAAGGGGTGTATGTCTGGGCGACCTTCGT

A  V  Q  S  I  C  N  A  L  G  V  P  H  I  Q  T  R  W  K  H -

CCAGGTGTCAGACAACAAAGATTCCTTCTATGTCAGTCTCTACCCAGACTTCTCTTCACT
541 ---------+---------+---------+---------+---------+---------+ 600
    GGTCCACAGTCTGTTGTTTCTAAGGAAGATACAGTCAGAGATGGGTCTGAAGAGAAGTGA

```
     CAGCCGTGCCATTTTAGACCTGGTGCAGTTTTTCAAGTGGAAAACCGTCACGGTTGTGTA
601  ------------------------------------------------------------  660
     GTCGGCACGGTAAAATCTGGACCACGTCAAAAAGTTCACCTTTTGGCAGTGCCAACACAT

S  R  A  I  L  D  L  V  Q  F  F  K  W  K  T  V  T  V  V  Y  -

TGATGACAGCACTGGTCTCATTCGTTTGCAAGAGCTCATCAAAGCTCCATCAAGGTATAA
661  ------------------------------------------------------------  720
     ACTACTGTCGTGACCAGAGTAAGCAAACGTTCTCGAGTAGTTTCGAGGTAGTTCCATATT

D  D  S  T  G  L  I  R  L  Q  E  L  I  K  A  P  S  R  Y  N  -

TCTTCGACTCAAAATTCGTCAGTTACCTGCTGATACAAAGGATGCAAAACCCTTACTAAA
721  ------------------------------------------------------------  780
     AGAAGCTGAGTTTTAAGCAGTCAATGGACGACTATGTTTCCTACGTTTTGGGAATGATTT

L  R  L  K  I  R  Q  L  P  A  D  T  K  D  A  K  P  L  L  K  -

AGAAATGAAAAGAGGCAAGGAGTTTCATGTAATCTTTGATTGTAGCCATGAAATGGCAGC
781  ------------------------------------------------------------  840
     TCTTTACTTTTCTCCGTTCCTCAAAGTACATTAGAAACTAACATCGGTACTTTACCGTCG

E  M  K  R  G  K  E  F  H  V  I  F  D  C  S  H  E  M  A  A  -

AGGCATTTTAAAACAGGCATTAGCTATGGGAATGATGACAGAATACTATCATTATATCTT
841  ------------------------------------------------------------  900
     TCCGTAAAATTTTGTCCGTAATCGATACCCTTACTACTGTCTTATGATAGTAATATAGAA

G  I  L  K  Q  A  L  A  M  G  M  M  T  E  Y  Y  H  Y  I  F  -

TACCACTCTGGACCTCTTTGCTCTTGATGTTGAGCCCTACCGATACAGTGGTGTTAACAT
901  ------------------------------------------------------------  960
     ATGGTGAGACCTGGAGAAACGAGAACTACAACTCGGGATGGCTATGTCACCACAATTGTA

T  T  L  D  L  F  A  L  D  V  E  P  Y  R  Y  S  G  V  N  M  -

GACAGGGTTCAGAATATTAAATACAGAAAATACCCAAGTCTCCTCCATCATTGAAAAGTG
961  ------------------------------------------------------------  1020
     CTGTCCCAAGTCTTATAATTTATGTCTTTTATGGGTTCAGAGGAGGTAGTAACTTTTCAC

T  G  F  R  I  L  N  T  E  N  T  Q  V  S  S  I  I  E  K  W  -

GTCGATGGAACGATTGCAGGCACCTCCGAAACCCGATTCAGGTTTGCTGGATGGATTTAT
1021 ------------------------------------------------------------  1080
     CAGCTACCTTGCTAACGTCCGTGGAGGCTTTGGGCTAAGTCCAAACGACCTACCTAAATA

S  M  E  R  L  Q  A  P  P  K  P  D  S  G  L  L  D  G  F  M  -

GACGACTGATGCTGCTCTAATGTATGATGCTGTGCATGTGGTGTCTGTGGCCGTTCAACA
1081 ------------------------------------------------------------  1140
     CTGCTGACTACGACGAGATTACATACTACGACACGTACACCACAGACACCGGCAAGTTGT

T  T  D  A  A  L  M  Y  D  A  V  H  V  V  S  V  A  V  Q  Q  -

GTTTCCCCAGATGACAGTCAGTTCCTTGCAGTGTAATCGACATAAACCCTGGCGCTTCGG
1141 ------------------------------------------------------------  1200
     CAAAGGGGTCTACTGTCAGTCAAGGAACGTCACATTAGCTGTATTTGGGACCGCGAAGCC

```
      GACCCGCTTTATGAGTCTAATTAAAGAGGCACATTGGGAAGGCCTCACAGGCAGAATAAC
1201  ------------+----------+----------+----------+----------+----------+  1260
      CTGGGCGAAATACTCAGATTAATTTCTCCGTGTAACCCTTCCGGAGTGTCCGTCTTATTG

T  R  F  M  S  L  I  K  E  A  H  W  E  G  L  T  G  R  I  T   -

TTTCAACAAAACCAATGGCTTGAGAACAGATTTTGATTTGGATGTGATCAGTCTGAAGGA
1261  ------------+----------+----------+----------+----------+----------+  1320
      AAAGTTGTTTTGGTTACCGAACTCTTGTCTAAAACTAAACCTACACTAGTCAGACTTCCT

F  N  K  T  N  G  L  R  T  D  F  D  L  D  V  I  S  L  K  E   -

AGAAGGTCTAGAAAAGATTGGAACGTGGGATCCAGCCAGTGGCCTGAATATGACAGAAAG
1321  ------------+----------+----------+----------+----------+----------+  1380
      TCTTCCAGATCTTTTCTAACCTTGCACCCTAGGTCGGTCACCGGACTTATACTGTCTTTC

E  G  L  E  K  I  G  T  W  D  P  A  S  G  L  N  M  T  E  S   -

TCAAAAGGGAAAGCCAGCGAACATCACAGATTCCTTATCCAATCGTTCTTTGATTGTTAC
1381  ------------+----------+----------+----------+----------+----------+  1440
      AGTTTTCCCTTTCGGTCGCTTGTAGTGTCTAAGGAATAGGTTAGCAAGAAACTAACAATG

Q  K  G  K  P  A  N  I  T  D  S  L  S  N  R  S  L  I  V  T   -

CACCATTTTGGAAGAGCCTTATGTCCTTTTTAAGAAGTCTGACAAACCTCTCTATGGTAA
1441  ------------+----------+----------+----------+----------+----------+  1500
      GTGGTAAAACCTTCTCGGAATACAGGAAAAATTCTTCAGACTGTTTGGAGAGATACCATT

T  I  L  E  E  P  Y  V  L  F  K  K  S  D  K  P  L  Y  G  N   -

TGATCGATTTGAAGGCTATTGCATTGATCTCCTCAGAGAGTTATCTACAATCCTTGGCTT
1501  ------------+----------+----------+----------+----------+----------+  1560
      ACTAGCTAAACTTCCGATAACGTAACTAGAGGAGTCTCTCAATAGATGTTAGGAACCGAA

D  R  F  E  G  Y  C  I  D  L  L  R  E  L  S  T  I  L  G  F   -

TACATATGAAATTAGACTTGTGGAAGATGGGAAATATGGAGCCCAGGATGATGCCAATGG
1561  ------------+----------+----------+----------+----------+----------+  1620
      ATGTATACTTTAATCTGAACACCTTCTACCCTTTATACCTCGGGTCCTACTACGGTTACC

T  Y  E  I  R  L  V  E  D  G  K  Y  G  A  Q  D  D  A  N  G   -

ACAATGGAATGGAATGGTTCGTGAACTAATTGATCATAAAGCTGACCTTGCAGTTGCTCC
1621  ------------+----------+----------+----------+----------+----------+  1680
      TGTTACCTTACCTTACCAAGCACTTGATTAACTAGTATTTCGACTGGAACGTCAACGAGG

Q  W  N  G  M  V  R  E  L  I  D  H  K  A  D  L  A  V  A  P   -

ACTGGCTATTACCTATGTTCGAGAGAAGGTCATCGACTTTTCCAAGCCCTTTATGACACT
1681  ------------+----------+----------+----------+----------+----------+  1740
      TGACCGATAATGGATACAAGCTCTCTTCCAGTAGCTGAAAAGGTTCGGGAAATACTGTGA

L  A  I  T  Y  V  R  E  K  V  I  D  F  S  K  P  F  M  T  L   -

TGGAATAAGTATTTTGTACCGCAAGCCCAATGGTACAAACCCAGGCGTCTTCTCCTTCCT
1741  ------------+----------+----------+----------+----------+----------+  1800
      ACCTTATTCATAAAACATGGCGTTCGGGTTACCATGTTTGGGTCCGCAGAAGAGGAAGGA

```
       GAATCCTCTCTCCCCTGATATCTGGATGTATATTCTGCTGGCTTACTTGGGTGTCAGTTG
1801   ----------+---------+---------+---------+---------+---------+ 1860
       CTTAGGAGAGAGGGGACTATAGACCTACATATAAGACGACCGAATGAACCCACAGTCAAC

N  P  L  S  P  D  I  W  M  Y  I  L  L  A  Y  L  G  V  S  C  -

TGTGCTCTTTGTCATAGCCAGGTTTAGTCCTTATGAGTGGTATAATCCACACCCTTGCAA
1861   ----------+---------+---------+---------+---------+---------+ 1920
       ACACGAGAAACAGTATCGGTCCAAATCAGGAATACTCACCATATTAGGTGTGGGAACGTT

V  L  F  V  I  A  R  F  S  P  Y  E  W  Y  N  P  H  P  C  N  -

CCCTGACTCAGACGTGGTGGAAAACAATTTTACCTTGCTAAATAGTTTCTGGTTTGGAGT
1921   ----------+---------+---------+---------+---------+---------+ 1980
       GGGACTGAGTCTGCACCACCTTTTGTTAAAATGGAACGATTTATCAAAGACCAAACCTCA

P  D  S  D  V  V  E  N  N  F  T  L  L  N  S  F  W  F  G  V  -

TGGAGCTCTCATGCAGCAAGGTTCTGAGCTCATGCCCAAAGCACTGTCCACCAGGATAGT
1981   ----------+---------+---------+---------+---------+---------+ 2040
       ACCTCGAGAGTACGTCGTTCCAAGACTCGAGTACGGGTTTCGTGACAGGTGGTCCTATCA

G  A  L  M  Q  Q  G  S  E  L  M  P  K  A  L  S  T  R  I  V  -

GGGAGGCATTTGGTGGTTTTTCACACTTATCATCATTTCTTCGTATACTGCTAACTTAGC
2041   ----------+---------+---------+---------+---------+---------+ 2100
       CCCTCCGTAAACCACCAAAAAGTGTGAATAGTAGTAAAGAAGCATATGACGATTGAATCG

G  G  I  W  W  F  F  T  L  I  I  I  S  S  Y  T  A  N  L  A  -

CGCCTTTCTGACAGTGGAACGCATGGAATCCCCTATTGACTCTGCTGATGATTTAGCTAA
2101   ----------+---------+---------+---------+---------+---------+ 2160
       GCGGAAAGACTGTCACCTTGCGTACCTTAGGGGATAACTGAGACGACTACTAAATCGATT

A  F  L  T  V  E  R  M  E  S  P  I  D  S  A  D  D  L  A  K  -

ACAAACCAAGATAGAATATGGAGCAGTAGAGGATGGTGCAACCATGACTTTTTTCAAGAA
2161   ----------+---------+---------+---------+---------+---------+ 2220
       TGTTTGGTTCTATCTTATACCTCGTCATCTCCTACCACGTTGGTACTGAAAAAAGTTCTT

Q  T  K  I  E  Y  G  A  V  E  D  G  A  T  M  T  F  F  K  K  -

ATCAAAAATCTCCACGTATGACAAAATGTGGGCCTTTATGAGTAGCAGAAGGCAGTCAGT
2221   ----------+---------+---------+---------+---------+---------+ 2280
       TAGTTTTTAGAGGTGCATACTGTTTTACACCCGGAAATACTCATCGTCTTCCGTCAGTCA

S  K  I  S  T  Y  D  K  M  W  A  F  M  S  S  R  R  Q  S  V  -

GCTGGTCAAAAGTAATGAAGAAGGAATCCAGCGAGTCCTCACCTCTGATTATGCTTTCCT
2281   ----------+---------+---------+---------+---------+---------+ 2340
       CGACCAGTTTTCATTACTTCTTCCTTAGGTCGCTCAGGAGTGGAGACTAATACGAAAGGA

L  V  K  S  N  E  E  G  I  Q  R  V  L  T  S  D  Y  A  F  L  -

AATGGAGTCAACAACCATCGAGTTTGTTACCCAGCGGAACTGTAACCTGACACAGATTGG
2341   ----------+---------+---------+---------+---------+---------+ 2400
       TTACCTCAGTTGTTGGTAGCTCAAACAATGGGTCGCCTTGACATTGGACTGTGTCTAACC

```
       CGGCCTTATAGACTCTAAAGGTTATGGCGTTGGCACTCCCATGGGTTCTCCATATCGAGA
2401   ------------+----------+----------+----------+----------+----------+ 2460
       GCCGGAATATCTGAGATTTCCAATACCGCAACCGTGAGGGTACCCAAGAGGTATAGCTCT

G  L  I  D  S  K  G  Y  G  V  G  T  P  M  G  S  P  Y  R  D  -

CAAAATTACCATAGCAATTCTTCAGCTGCAAGAGGAAGGCAAACTGCATATGATGAAGGA
2461   ------------+----------+----------+----------+----------+----------+ 2520
       GTTTTAATGGTATCGTTAAGAAGTCGACGTTCTCCTTCCGTTTGACGTATACTACTTCCT

K  I  T  I  A  I  L  Q  L  Q  E  E  G  K  L  H  M  M  K  E  -

GAAATGGTGGAGGGGCAATGGTTGCCCAGAAGAGGAAAGCAAAGAGGCCAGTGCCCTGGG
2521   ------------+----------+----------+----------+----------+----------+ 2580
       CTTTACCACCTCCCCGTTACCAACGGGTCTTCTCCTTTCGTTTCTCCGGTCACGGGACCC

K  W  W  R  G  N  G  C  P  E  E  E  S  K  E  A  S  A  L  G  -

GGTTCAGAATATTGGTGGCATCTTCATTGTTCTGGCAGCCGGCTTGGTGCTTTCAGTTTT
2581   ------------+----------+----------+----------+----------+----------+ 2640
       CCAAGTCTTATAACCACCGTAGAAGTAACAAGACCGTCGGCCGAACCACGAAAGTCAAAA

V  Q  N  I  G  G  I  F  I  V  L  A  A  G  L  V  L  S  V  F  -

TGTGGCAGTGGGAGAATTTTTATACAAATCCAAAAAAAACGCTCAATTGGAAAAGAGGTC
2641   ------------+----------+----------+----------+----------+----------+ 2700
       ACACCGTCACCCTCTTAAAAATATGTTTAGGTTTTTTTGCGAGTTAACCTTTTCTCCAG

V  A  V  G  E  F  L  Y  K  S  K  K  N  A  Q  L  E  K  R  S  -

CTTCTGTAGTGCCATGGTAGAAGAATTGAGGATGTCCCTGAAGTGCCAGCGTCGGTTAAA
2701   ------------+----------+----------+----------+----------+----------+ 2760
       GAAGACATCACGGTACCATCTTCTTAACTCCTACAGGGACTTCACGGTCGCAGCCAATTT

F  C  S  A  M  V  E  E  L  R  M  S  L  K  C  Q  R  R  L  K  -

ACATAAGCCACAGGCCCCAGTTATTGTGAAAACAGAAGAAGTTATCAACATGCACACATT
2761   ------------+----------+----------+----------+----------+----------+ 2820
       TGTATTCGGTGTCCGGGGTCAATAACACTTTTGTCTTCTTCAATAGTTGTACGTGTGTAA

H  K  P  Q  A  P  V  I  V  K  T  E  E  V  I  N  M  H  T  F  -

EcoRI
                                                               |
       TAACGACAGAAGGTTGCCAGGTAAAGAAACCATGGCATAAAGCTGGGAGGCGGAATTC
2821   ------------+----------+----------+----------+----------+--------- 2878
       ATTGCTGTCTTCCAACGGTCCATTTCTTTGGTACCGTATTTCGACCCTCCGCCTTAAG

N  D  R  R  L  P  G  K  E  T  M  A  *
``` humEAA4a (SEQ ID NO:3)   2376 GGAACTGTAACCTGTGACACAGATTGGGCGGCCTTATAGACTCTAAAGGTTAT 2425
                              ||||||||||||||||||||||||||||||||||||||||||||||||||||
humEAA4b (SEQ ID NO:4)   2376 GGAACTGTAACCTGTGACACAGATTGGCGACCTTATAGACTCTAAAGGTTAT 2425 humEAA4a (SEQ ID NO:5)    700 SDYAFLMESTTIEFVTQRNCNLTQIGGLIDSKGYGVGTPMGSPYRDKITI 750
                              |||||||||||||||||||||||||| |||||||||||||||||||||
humEAA4b (SEQ ID NO:6)    700 SDYAFLMESTTIEFVTQRNCNLTQIGDLIDSKGYGVGTPMGSPYRDKITI 750

FIG. 3A humEAA4a (SEQ ID NO:7)    1971 GGTTTGGAGTTGGAGCTCTCATGCAGCAAGGTTCTGAGCTCATGCCCAAA 2020
                               |||||||||||||||||||||||||||||||||||||||||||||||||
humEAA4a-1 (SEQ ID NO:8)  1971 GGTTTGGAGTTGGAGCTCTCATGCAACAAGGTTCTGAGCTCATGCCCAAA 2020

FIG. 3B

[³H] KAINATE BINDING humEAA4a $5 \times 10^{-8}$ M KAINATE AT
$-70$ mV • (1000us)

KAINATE-BINDING, HUMAN CNS RECEPTORS OF THE EAA4 FAMILY

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND OF THE INVENTION

In the mammalian central nervous system (CNS), the transmission of nerve impluses is controlled by the interaction between a neurotransmitter substance, released by the "sending" neuron, and a surface receptor on the "receiving" neuron to which it binds, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered. Hollmann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettier et al., Neuron 5: 583. 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gene. These authors, as well as Monyer et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

Some recent work has also been published regarding non-human genes which appear to encode the kainate-type of receptor. Egebjerg et al., Nature 351: 745, 1991, have described the isolation of a gene from rat called GluR6, which although related in sequence to the AMPA receptor genes, forms a receptor which is not activated by AMPA but rather by glutamate, quisqualate, and preferentially, kainate. Other kainate-binding proteins have been described from frog (Wada et al., Nature 342: 684, 1989), chicken (Gregor et al., Nature 342: 689, 1989) and from rat (Werner et al., Nature 351: 742, 1991). These latter genes encode proteins which bind kainate, but which do not readily form into functional ion channels when expressed by themselves.

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Genes coding for a family of EAA receptors endogenous to human brain have now been identified and characterized. A representative member of this human EAA receptor family, designated human EAA4a, codes for a receptor protein that in addition to binding glutamate with an affinity typical of EAA receptors, also exhibits ligand binding properties characteristic of kainate-type EAA receptors. Sequence-related genes coding for naturally occurring variants of the human EAA4a receptor have also been identified, and constitute additional members of this receptor family, herein referred to as the human EAA4 receptor family.

The present invention thus provides, in one of its aspects, an isolated polynucleotide, consisting either of DNA or of RNA, which codes for a human EAA4 receptor or for a kainate-binding fragment thereof.

In another aspect of the present invention, there is provided a cell that has been genetically engineered to produce a kainate-binding, human EAA receptor belonging to the herein-defined EAA4 family. In related aspects of the present invention, there are provided recombinant DNA constructs and relevant methods useful to create such cells.

In another aspect of the present invention, there is provided a method for evaluating interaction between a test ligand and a human EAA receptor, which comprises the steps of incubating the test ligand with a genetically engineered cell of the present invention, or with a membrane preparation derived therefrom, and then assessing said interaction by determining one of receptor/ligand binding and ligand-mediated ion channel activation.

Other aspects of the present invention, which encompass various applications of the discoveries herein described, will become apparent from the following detailed description, and from the accompanying drawings, in which:

BRIEF DESCRIPTION OF THE DRAWINGS

FIGS. 1A–1E provide the nucleotide sequence (SEQ ID NO: 1) of DNA coding for an excitatory amino acid receptor of the present invention, and the deduced amino acid sequence (SEQ ID NO: 2) thereof;

FIGS. 3A and 3B show, with reference to FIG. 1 (these sequences are also shown in SEQ ID NOS: 3–8), the DNA and amino acid sequences of naturally occurring variants of the EAA receptor illustrated in FIGS. 1A–1E.

DETAILED DESCRIPTION OF THE INVENTION AND ITS PREFERRED EMBODIMENTS

Figure 2:
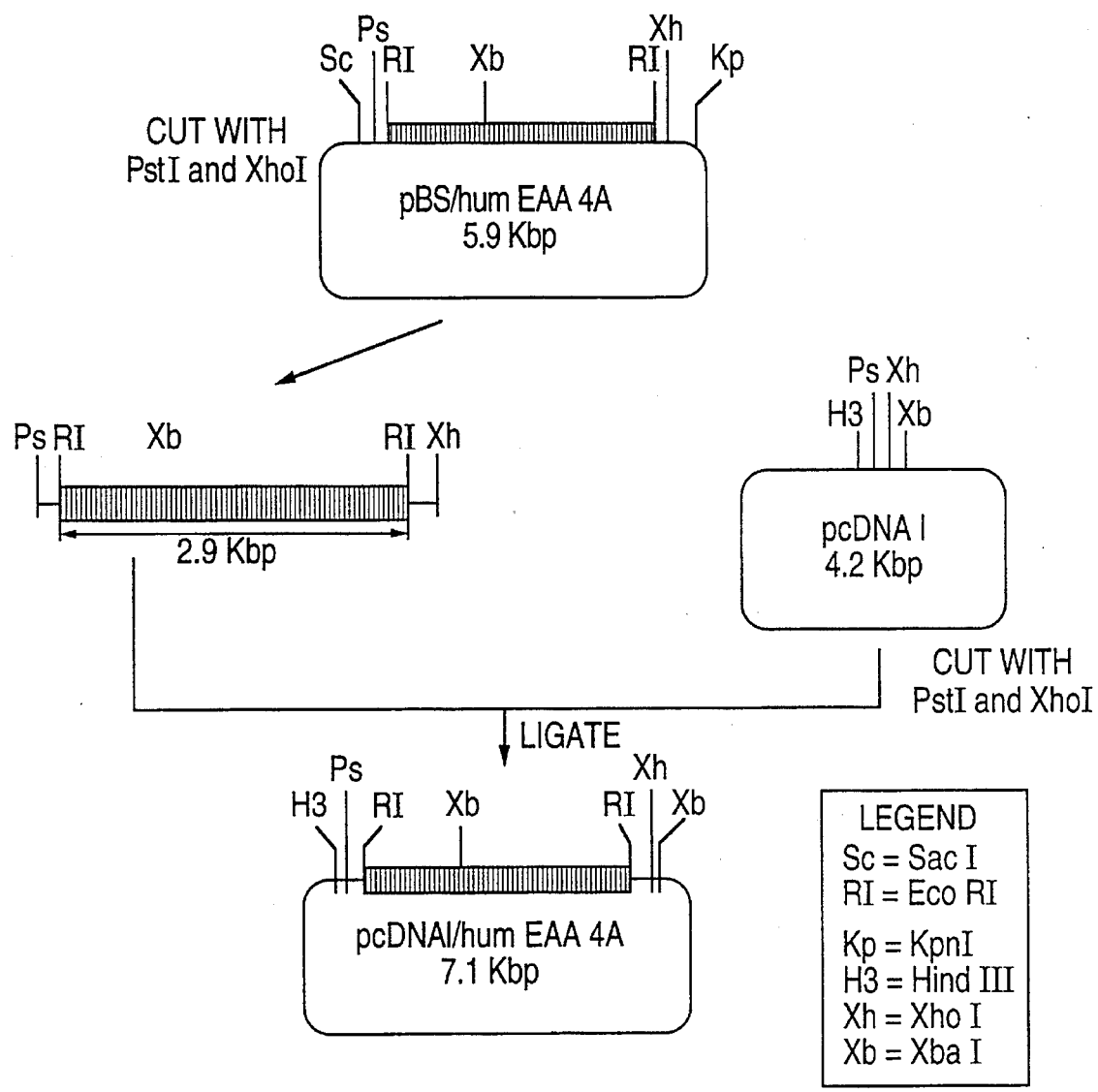
FIG. 2 illustrates with linear plasmid maps the strategy used to construct expression vectors harbouring the DNA sequence illustrated in FIGS. 1A–1E.

The invention relates to excitatory amino acid (EAA) receptors of human origin, and is directed more particularly to a novel family of kainate-type human EAA receptors, herein designated the human EAA4 receptor family. As used herein, the term "human EAA4 receptor" is intended to embrace the human EAA4a receptor, and kainate-binding variants of the EAA4a receptor that are structurally related thereto, i.e. share at least 98% amino acid identity, including naturally occurring and synthetically derived variants of the EAA4a receptor. Naturally occurring variants of the human EAA4a receptor include particularly the receptors herein designated human EAA4b receptor. Synthetically derived variants of the human EAA4a receptor include kainate-binding variants that incorporate one or more, e.g. 1–10, amino acid substitutions, deletions or additions, relative to the EAA4a receptor.

As used herein, the term "kainate-binding" refers to receptor variants and receptor fragments that display greater binding affinity for kainate than for either glutamate, AMPA or NMDA, as determined in assays of conventional design, such as the assays herein described.

Each of the naturally occurring members of the EAA4 receptor family possesses structural features characteristic of the EAA receptors in general, including extracellular N- and C-terminal regions, as well as four internal hydrophobic domains which serve to anchor the receptor within the cell surface membrane. The particular human EAA receptor designated EAA4a is a protein characterized structurally as a single polypeptide chain that is produced initially in precursor form bearing a 31 residue N-terminal signal peptide, and is transported to the cell surface in mature form, lacking the signal peptide and consisting of 877 amino acids arranged in the sequence illustrated, by single letter code, in FIG. 1 and SEQ ID NOS: 1 and 2. Unless otherwise stated, the term "EAA4 receptor" refers to the mature form of the receptor protein, and amino acid residues of the EAA4 receptors are accordingly numbered with reference to the mature protein sequence. With respect to structural domains of the receptor, hydropathy analysis reveals four putative transmembrane domains, one spanning residues 532–551 inclusive (TM-1), another spanning residues 575–593 (TM-2), a third spanning residues 604–622 (TM-3) and the fourth spanning residues 789–809 (TM-4). Based on this assignment, it is likely that the human EAA4a receptor structure, in its natural membrane-bound form, consists of a 531 amino acid N-terminal extracellular domain, followed by a hydrophobic region containing four transmembrane domains and an extracellular, 68 amino acid C-terminal domain.

As shown in FIG. 3 and SEQ ID NOS. 3–8, a structurally related variant of the EAA4a receptor, which occurs naturally in human brain tissue, has also been identified and is designated the EAA4b receptor. As deduced from nucleotide sequences of the genes coding for them, the EAA4b variant shares greater than 99% amino acid identity with EAA4a, differing with respect only to a single amino acid change at position 727, which in the EAA4a receptor is a glycine residue and in the EAA4b receptor is an aspartic acid residue.

In human fetal brain cDNA libraries, the source from which DNA coding for the EAA4a receptor was isolated, the EAA4a receptor is encoded by the nucleotide sequence provided in FIGS. 1A–1E SEQ ID NO: 1. Also isolated during probing of the cDNA library was a polynucleotide variant of the sequence shown in FIGS. 1A–1E SEQ ID NO: 1, designated EAA4a-1, which incorporates a codon different from, but synonymous with, the triplet coding for glutamine at position 621 (see FIG. 3A SEQ ID NOS. 3–8). It will thus be appreciated that the EAA4a receptor may of course be encoded by polynucleotides incorporating codons synonymous with those illustrated in FIGS. 1A–1E SEQ ID NO: 1.

Relative to EAA receptors previously discovered in rat tissue, as described in the publications mentioned hereinabove, members of the human EAA4 receptor family share not greater than about 98% amino acid identity with such rat receptors, with the greatest identity of about 97% being shared with the rat GluR6 receptor reported recently by Egebjerg et al, supra. The human EAA4 receptors differ most significantly from this rat receptor in the extracellular, C-terminal region of the receptors which, in the human receptors, is extended by an additional 25 amino acids.

Like other members of the human EAA4 receptor family, receptor subtype EAA4a is characterized by a pharmacological profile i.e. a ligand binding "signature", that points strongly to a kainate-type pharmacology, as distinct from other excitatory amino acid receptor types, such as NMDA and AMPA. In addition and despite the understanding that kainate binding receptors require a multi- and perhaps heteromeric subunit structure to function in the pharmacological sense, it has been found that cells producing the unitary EAA4a receptor do, independently of association with other receptor subunits, provide a reliable indication of excitatory amino acid binding and also channel activation. Thus, in a key aspect of the present invention, the human EAA4a receptor is exploited for the purpose of screening candidate compounds for the ability to interact with the present receptors and/or the ability to compete with endogenous EAA receptor ligands and known synthetic analogues thereof, for EAA receptor interaction.

For use in assessing interaction between the receptor and a test ligand, it is desirable to construct by application of genetic engineering techniques a mammalian cell that produces a human EAA4 receptor in functional form as a heterologous product. The construction of such cell lines is achieved by introducing into a selected host cell a recombinant DNA construct in which DNA coding for a secretable form of the human EAA4 receptor, i.e., a form bearing either its native signal peptide or a functional, heterologous equivalent thereof, is associated with expression controlling elements that are functional in the selected host to drive expression of the receptor-encoding DNA, and thus elaborate the desired EAA4 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host.

The particular cell type selected to serve as host for production of the human EAA4 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevertheless serve as expression hosts, provided that "background" binding to the test ligand is accounted for in the assay results.

According to one embodiment of the present invention, the cell line selected to serve as host for EAA4 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the EAA4 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for a secretable form of the receptor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as *E.coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals, i.e., the metalothionein gene promoter, and other steroid-inducible promoters.

For incorporation into the recombinant DNA expression vector, DNA coding for the desired EAA4 receptor, e.g. the EAA4a receptor or a kainate-binding variant thereof, can be obtained by applying selected techniques of gene isolation or gene synthesis. As described in more detail in the examples herein, the EAA4a receptor, and the EAA4b variant thereof, are encoded within the genome of human brain tissue, and can therefore be obtained by careful application of conventional gene isolation and cloning techniques. This typically will entail extraction of total messenger RNA from a fresh source of human brain tissue, such as cerebellum or hippocampus tissue and preferably fetal brain tissue, followed by conversion of message to cDNA and formation of a library in, for example, a bacterial plasmid, more typically a bacteriophage. Such bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA4 receptors, it will be appreciated that automated techniques of gene synthesis and/or amplification can be performed to generate DNA coding therefor. Because of the length of EAA4 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA4 gene family. It will be appreciated, for example and as mentioned above, that polynucleotides coding for the EAA4 receptors herein described can be generated by substituting synonymous codons for those represented in the naturally occurring polynucleotide sequences herein identified. In addition, polynucleotides coding for synthetic variants of the EAA4 receptors herein described can be generated which, for example incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity, e.g., within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, microinjection, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the *E. coli* gpt gene which confers resistance to mycophenolic acid, the neogene from transposon Tn5 which confers resistance to the antibiotic G418 and to neomycin, the dhfr sequence from murine cells or *E. coli* which changes the phenotype of DHFR–cells into DHFR+cells, and the tk gene of herpes simplex virus, which makes TK–cells phenotypically TK+cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human EAA4 receptor of the invention is evaluated typically using a predetermined amount of cell-derived membrane (measured for example by protein determination), generally from about 25 µg to 100 µg. Generally, competitive binding assays will be useful to evaluate the affinity of a test compound relative to kainate. This competitive binding assay can be performed by incubating the membrane preparation with radiolabelled kainate, for example [$^3$H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

The EAA4 receptors of the present invention are per se functional in an electrophysiological context, and are therefore useful, in the established manner, in screening test ligands for their ability to modulate ion channel activity. The present invention thus further provides, as a ligand screening technique, the method of detecting interaction between a test ligand and a human CNS receptor, which comprises the steps of incubating the test ligand with a human EAA4 receptor-producing cell or with a membrane preparation derived therefrom, and then measuring ligand-induced electrical current across said cell or membrane.

As an alternative to using cells that express receptor-encoding DNA, ligand characterization, either through binding or through ion channel formation, may also be performed using cells, for example Xenopus oocytes, that yield functional membrane-bound receptor following introduction of messenger RNA coding for the EAA4 receptor. In this case, the EAA4 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell or placed on either side of a cell-derived membrane preparation, using the so-called "patch-clamp" technique.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the EAA4 receptor responsible for binding a ligand molecule resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length EAA4 receptor-encoding DNA may be modified by site-directed mutagenesis, so as to introduce a translational stop codon into the extracellular N-terminal region, immediately before the sequence encoding the first transmembrane domain (TM1), i.e., before residue 532 as shown in FIGS. 1A–1E SEQ ID NOS. 1 and 2. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 810 and 877 inclusive of FIGS. 1A–1E SEQ ID NOS. 1 and 2. In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. *Aspergillus nidulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of an EAA4 receptor, for example in brain tissue, the present invention also provides, in another of its aspects, labelled antibody to a human EAA4 receptor. To raise such antibodies, there may be used as immunogen either the intact, soluble receptor or an immunogenic fragment thereof, produced in a microbial or mammalian cell host as described above or by standard peptide synthesis techniques. Regions of the EAA4a receptor particularly suitable for use as immunogenic fragments include those corresponding in sequence to an extracellular region of the receptor, or a portion of the extracellular region, such as peptides consisting of residues 1–531, including particularly residues 184–199 or 484–527, and peptides corresponding to the region between transmembrane domains TM-2 and TM-3, such as a peptide consisting of residues 594–603. Peptides consisting of the C-terminal domain (residues 810–877), or fragment thereof such as a peptide consisting of residues 850–877 may also be used for the raising of antibodies. Substantially the same region of the human EAA4b receptor may also be used for production of antibodies against this receptor.

The raising of antibodies to the desired EAA4 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for the human EAA4 receptor, and selected regions thereof, may also be used, in accordance with another aspect of the present invention, as hybridization probes, for example to identify sequence-related genes resident in the human or other mammalian genomes (or cDNA libraries) or to locate the EAA4-encoding DNA in a specimen, such as brain tissue. This can be done using either the intact coding region, or a fragment thereof having radiolabelled e.g. $^{32}P$, nucleotides incorporated therein. To identify the EAA4-encoding DNA in a specimen, it is desirable to use either the full length cDNA coding therefor, or a fragment which is unique thereto. With reference to FIGS. 1A–1E SEQ ID NO: 1 and the nucleotide numbering appearing thereon, such fragments include those comprising at least about 17 nucleotides, and otherwise corresponding in sequence to a region coding for the N-terminus or C-terminus of the receptor, or representing a 5'-untranslated or 3'-untranslated region thereof, such as one of the following nucleotide regions: 58–77, 148–165, 347–364, 806–823, 1986–2004, 2395–2413 and 2756–2773 (FIG. 1 SEQ ID NO: 1). These sequences, and the intact gene itself, may also be used of course to clone EAA4-related human genes, particularly cDNA equivalents thereof, by standard hybridization techniques.

EXAMPLE 1

Isolation of DNA Coding for the Human EAA4a Receptor cDNA coding for the human EAA4a receptor was identified by probing human fetal brain cDNA that was obtained as an EcoRI-based lambda phage library (lambda ZAP) from Stratagene Cloning Systems (La Jolla, Calif., U.S.A.). The cDNA library was screened using an oligonucleotide probe capable of annealing to the 3' region of the rat GluR5 receptor sequence reported by Bettier et al, supra. The specific sequence of the $^{32}P$-labelled probe is provided below:

5'SEQ ID NO: 9-ATCGGCGGCATCTTCATTGTTCTGGCTG-CAGGACTCGTGC-3'

The fetal brain cDNA library was screened under the following hybridization conditions; 6×SSC, 25% formamide, 5% Denhardt's solution, 0.5% SDS, 100 µg/ml denatured salmon sperm DNA, 42° C. Filters were washed with 2×SSC containing 0.5% SDS at 25° C. for 5 minutes; followed by a 15 minute wash at 50° C. with 2×SSC containing 0.5% SDS. The final wash was with 1×SSC containing 0.5% SDS at 50° C. for 15 minutes. Filters were exposed to X-ray film (Kodak) overnight. Of $10^6$ clones screened, only one cDNA insert, of about 2.9 kb, was identified, and designated RKCS5F94. For sequencing, the '94 phage was plaque purified, then excised as a phagemid according to the supplier's specifications, to generate an insert-carrying Bluescript-SK variant of the phagemid vector. Sequencing of the '94 clone across its entire sequence revealed a putative ATG initiation codon together with about 133 bases of 5' non-coding region and 2,724 bases of coding region. Also revealed was a termination codon, as well as about 18 bases of 3' non-translated sequence. The entire sequence of the EcoRI/EcoRI insert is provided in FIGS. 1A–1E SEQ ID NO: 1.

A 5.9 kb phagemid designated pBS/humEAA4a, carrying the receptor-encoding DNA as a 2.9 kb EcoRI/EcoRI insert in a 3.0 kb Bluescript-SK phagemid background, was deposited, under the terms of the Budapest Treaty, with the American Type Culture Collection in Rockville, Md. U.S.A. on May 28, 1992, and has been assigned accession number ATCC 75245.

EXAMPLE 2

Construction of Genetically Engineered Cells Producing the Human EAA4a Receptor

For transient expression in mammalian cells, cDNA coding for the human EAA4a receptor was incorporated into the mammalian expression vector pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The strategy depicted in FIG. 2 was employed to facilitate incorporation of the EAA4a receptor-encoding cDNA into an expression vector. The cDNA insert was released from pBS/humEAA4a as a 2.9 kb PstI/XhoI fragment, which was then incorporated at the PstI/XhoI sites in the pcDNAI polylinker. Sequencing across the junctions was performed, to confirm proper insert orientation in pcDNA1. The resulting plasmid, designated pcDNA1/humEAA4a, was then introduced for transient expression into a selected mammalian cell host, in this case the monkey-derived, fibroblast-like cells of the COS-1 lineage (available from the American Type Culture Collection, Rockville, Md. as ATCC CRL 1650).

For transient expression of the EAA4a-encoding DNA, COS-1 cells were transfected with approximately 8 µg DNA (as pcDNA1/humEAA4a) per $10^6$ COS cells, by DEAE-mediated DNA transfection and treated with chloroquine according to the procedures described by Maniatis et al, supra. Briefly, COS-1 cells were plated at a density of $5 \times 10^6$ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 µM chloroquine, 10% NuSerum, DNA (0.4 mg/ml)in DMEM/F12 medium. After incubation for 3 hours at 37° C., cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also be prepared using two different cell types as host: CHO K1 and CHO Pro5. To construct these cell lines, cDNA coding for human EAA4a is incorporated into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5 \times 10^5$ in 10% FBS-supplemented αMEM medium. After growth for 24 hours, fresh medium is added to the plates and three hours later, the cells are transfected using the calcium phosphate-DNA co-precipitation procedure (Maniatis et al, supra). Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 3

Ligand Binding Assays

Transfected cells in the frozen state were resuspended in ice-cold distilled water using a hand homogenizer and centrifuged for 20 minutes at 50,000 g. The supernatant was discarded and the membrane pellet stored frozen at −70° C.

COS cell membrane pellets were suspended in ice cold 50 mM Tris-HCl (pH 7.55, 5° C.) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation was used as tissue source for binding experiments described below. Proteins were determined using the Pierce Reagent with BSA as standard.

Binding assays were then performed, using an amount of COS-derived membrane equivalent to 25–100 μg as judged by protein determination and selected radiolabelled ligand. In particular, for kainate binding assays, incubation mixtures consisted of 25–100 μg tissue protein and [vinylidene-$^3$H] kainic acid (58 Ci/mmole, 85 nM final) in the cold incubation buffer, 1 ml final volume. Non-specific binding was in the presence of 1 mM L-glutamate. Samples were incubated on ice for 60 minutes, and bound and free ligand were then separated by rapid filtration using a PHD cell harvester and GF/B filters pre-soaked in ice-cold 0.3% polyethyleneimine. Filters were washed twice in 4 ml of the cold incubation buffer, then placed in scintillation vials with 5 ml of Beckman Ready-Protein Plus scintillation cocktail for counting.

For AMPA-binding assays, incubation mixtures consisted of 25–100 μg tissue protein and D,L-alpha-[5-methyl-3H] amino-3-hydroxy-5-methylisoxazole-4-propionic acid (3H-AMPA, 27.6 Ci/mmole, 10 nM final) with 0.1M KSCN and 2.5 mM CaCl$_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 4 ml of the cold incubation buffer, then 5 ml of Beckman Ready-Protein Plus scintillation cocktail was added, for counting.

Figure 4:
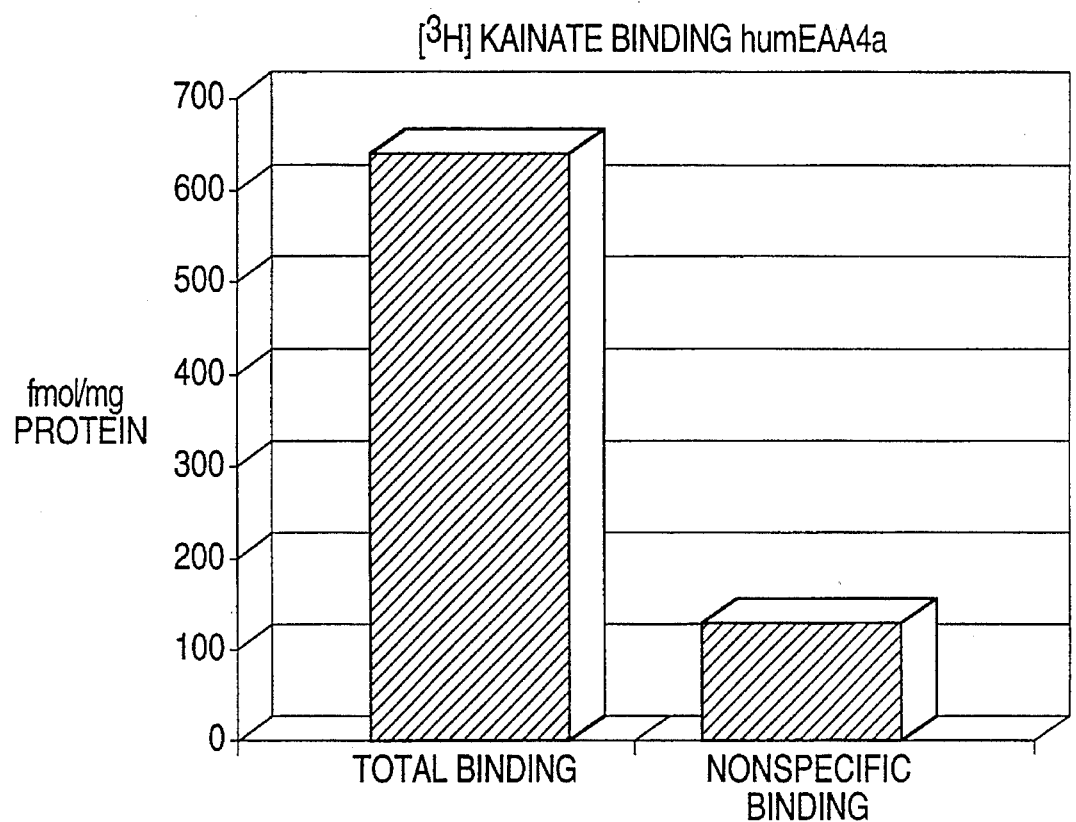
FIGS. 4–10 illustrate ligand-binding and channel activating properties of the EAA receptor expressed from the coding region provided in FIGS. 1A–1E.

Assays performed in this manner, using membrane preparations derived from the EAA4a-producing COS cells, revealed specific [$^3$H]-kainate binding at 85 nM, labelled ligand (FIG. 4). Mock transfected cells exhibited no specific binding of any of the ligands tested. These results demonstrate clearly that the human EAA4a receptor is binding kainate specifically. This activity, coupled with the fact that there is little or no demonstrable binding of either AMPA or NMDA clearly assigns the EAA4a receptor to be of the kainate type of EAA receptor. Furthermore, this binding profile indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA4a receptor gene in a pure form, capable of being expressed as a single, homogenous receptor species, therefore frees the ligand binding assay from the lack of precision introduced when complex, heterogeneous receptor preparations from human brains are used to attempt such characterizations.

EXAMPLE 4

Channel Activity Assays

Xenopus oocytes (stage V or VI) were harvested and the nuclei of the oocytes were injected with 5 ng of pcDNAI/humEAA4a DNA. The oocytes were then tested each day using a two-electrode voltage clamp, according to the method reported by Verdoorn et al, Mol. Pharmacol., 1988, 34:298. Successful expression occurred from day 5 onward.

Figure 5:
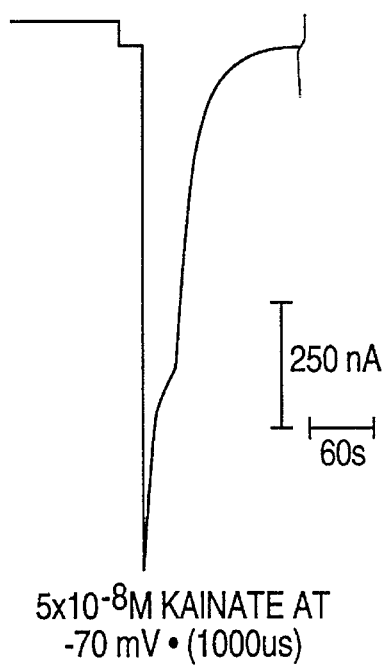

Oocytes injected with pcDNAI/humEAA4a and held at −100 mV responded to kainate. The application of kainate at concentrations greater than $5 \times 10^{-8}$M evoked large inward currents (>2000 nA) that rapidly desensitized in the continuing presence of agonist (FIG. 5). Full recovery from desensitization caused by 60 second application of kainate required approximately 10 minutes, although at high concentrations (>$10^{-4}$M), full recovery from desensitization required 15–20 minutes.

Figure 6:
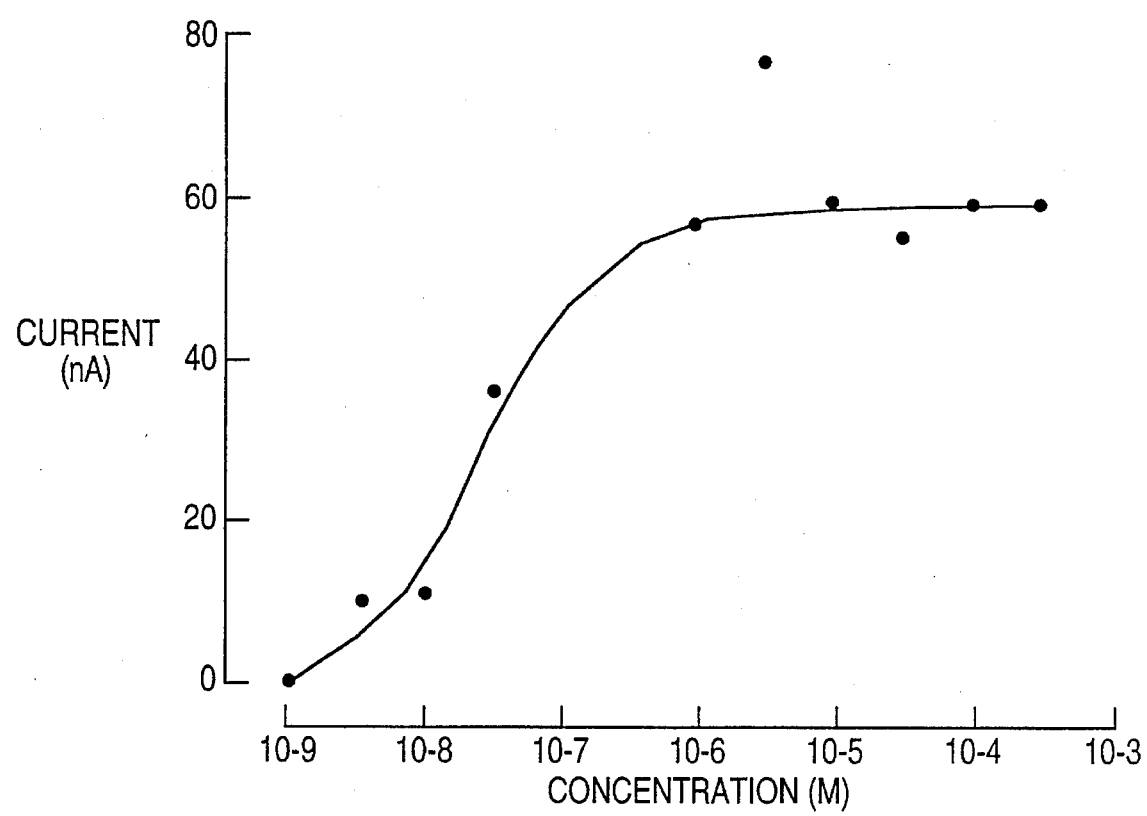

Because of the very large currents induced by the expression of humEAA4a, a dose-response curve for kainate was constructed at the unusually low holding membrane potential of −30 mV (FIG. 6). The concentration of kainate needed to evoke 50% of the maximal response (EC$_{50}$) was about $5 \times 10^{-8}$M which is considerably lower than the EC$_{50}$ of $10^{-6}$M reported by Egejberg et al, supra, for the kainate-binding rat receptor, GluR6.

Figure 7:
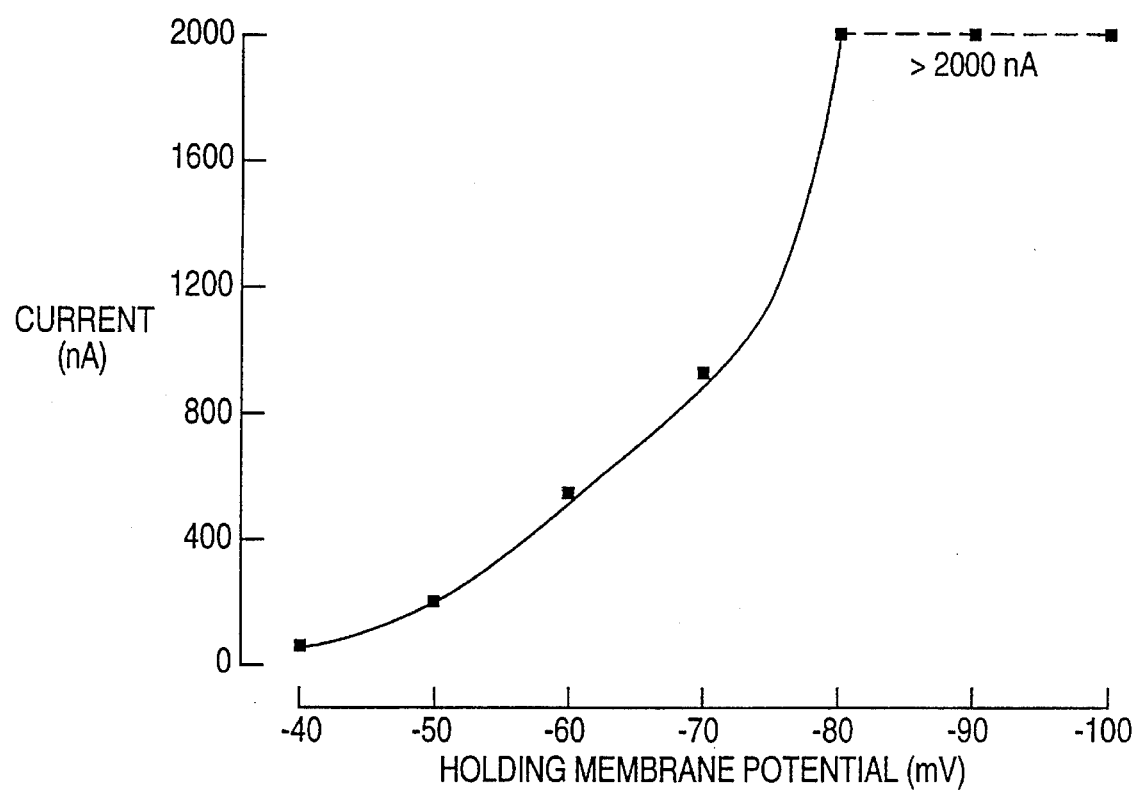

The current/voltage (I/V) relationship (FIG. 7) was constructed using $5 \times 10^{-8}$M kainate. The I/V relationship was non-linear and exhibiting a strong rectification. It was not possible to reverse the kainate induced currents, although the current disappeared at −10 reV. Furthermore, the currents recorded in oocytes after day 6 were always larger than 2000 nA at membrane potentials greater than −80 mV.

Figure 8:
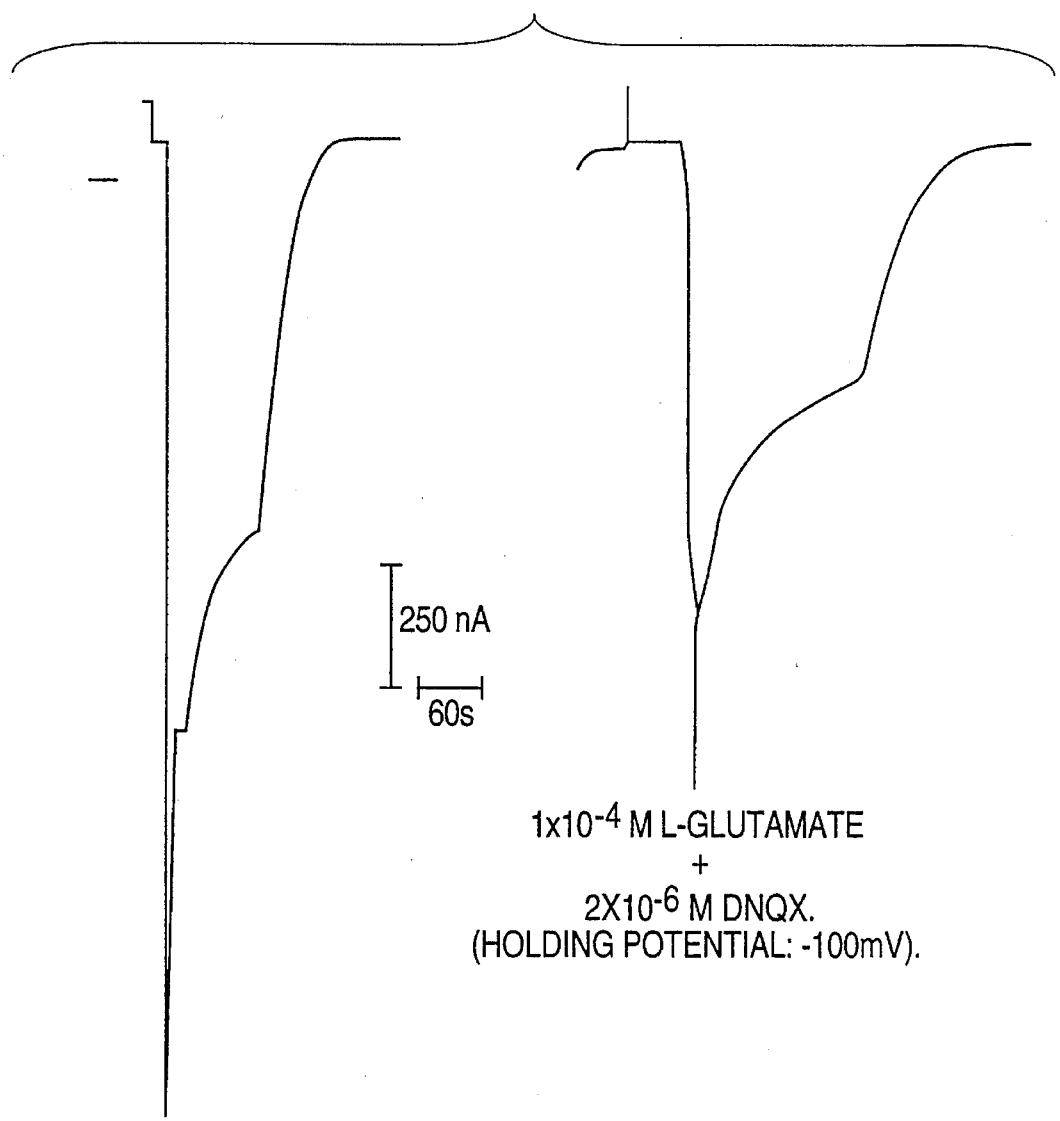

Exposure of the oocytes to L-glutamate induced smaller currents than kainate, which also rapidly desensitized in the continuing presence of glutamate (FIG. 8). Full recovery from desensitization following 60 second exposure to glutamate required approximately 5 minutes at concentrations below $10^{-4}$M and approximately 10 minutes at concentrations above $10^{-4}$M.

Figure 10:
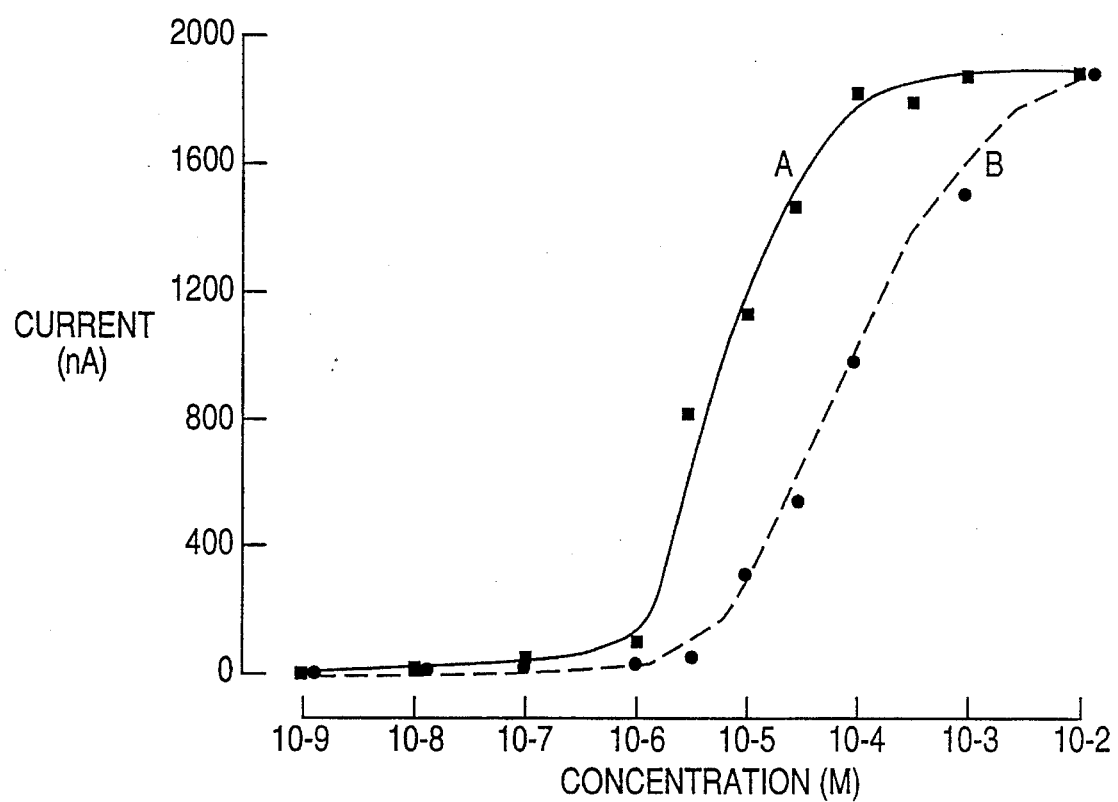

Because currents evoked by L-glutamate were smaller than those evoked by kainate, it was possible to construct a dose-response curve at a holding potential of −100 mV (FIG. 10). The concentration of L-glutamate required to evoke 50% of the maximal response ($EC_{50}$) was $5 \times 10^{-6}$M, as compared with $3.1 \times 10^{-5}$M reported for the rat GluR6 receptor (Egebjerg et al, supra).

DNQX (6,7-dinitroquinoxaline-2,3-dione) which is an antagonist of non-NMDA receptors blocked the glutamate response (FIG. 8) in a competitive manner. At a concentration of $2 \times 10^{-6}$M, DNQX caused a parallel shift of the dose/response curve for L-glutamate to the right (FIG. 10).

Figure 9:
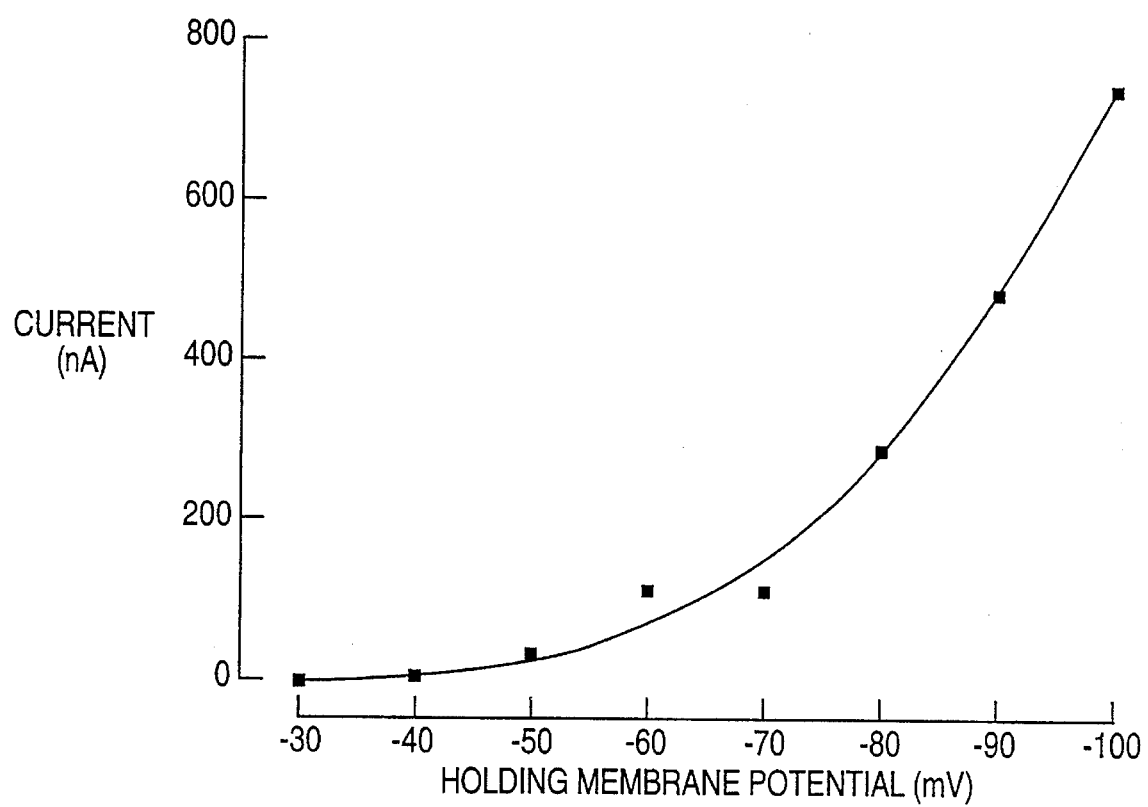

A current-voltage relationship was also constructed for $10^{-4}$M L-glutamate. The I/V relationship for L-glutamate (as for kainate) was strongly rectified (FIG. 9).

Oocytes did not respond to AMPA ($10^{-4}$M), NMDA ($10^{-4}$M), or NMDA ($10^{-4}$M) with glycine ($10^{-6}$M), when tested at −60, −80 and −100 mV.

The electrophysiological properties observed in oocytes following injection of pcDNAI/humEAA4a DNA into the nucleus, as well as the observed ligand binding pharmacological profile, indicate that humEAA4a receptor is per se sufficient, in the absence of other receptor complex components that may exist naturally, to form an active receptor/ion channel complex.

These electrophysiological and pharmacological properties of human EAA4 receptors indicate that the receptor ion-channel complex is functioning in an authentic manner and can therefore reliably predict the electrophysiological properties and ligand binding signature of its non-recombinant counterpart from the intact human brain. These features make the recombinant receptor especially useful for selecting and characterizing functional ligand compounds which can modulate, or effect, an ion channel response of these receptors. Additionally, these receptor/ion channel complexes can be used to identify and characterize test ligands that can block the ion channel function. The isolation of the human EAA4 receptor gene in a pure form, capable of being expressed as a single, homogeneous receptor/ion channel complex, therefore frees the functional ligand assay from the lack of precision introduced when complex, heterogeneous receptor preparations from human brain, and from model mammalian systems such as rat, are used to attempt such characterizations.

We claim:

1. An isolated polynucleotide that codes for the human EAA4 receptor that has the amino acid sequence of amino acids 1–877 of SEQ ID NO: 2.

2. An isolated polynucleotide that has the nucleotide sequence of nucleotides 226–2855 of SEQ ID NO: 1.

3. An isolated polynucleotide which encodes the human EAA4 receptor that has an amino acid sequence of amino acids 1–877 of SEQ ID NO: 2 with the exception that the amino acid at position 727 is aspartic acid, wherein said human EAA4 receptor is the human EAA4b receptor.

4. An isolated polynucleotide that has the nucleotide sequence of 226–2855 of SEQ ID NO: 1 with the exception that the guanosine at position 2403 is replaced by adenosine.

5. An oligonucleotide consisting of from 17 to 2634 nucleotides wherein said oligonucleotide is fully complementary to the polynucleotide as defined in claim 3.

6. An oligonucleotide according to claim 5, having a reporter molecule conjugated thereto.

7. An oligonucleotide as claimed in claim 5, consisting of from 17 to 40 nucleotides.

8. An oligonucleotide as claimed in claim 5, consisting of from 17 to 20 nucleotides.

9. An oligonucleotide consisting of from 17 to 2634 nucleotides wherein said oligonucleotide is fully complementary to a polynucleotide as defined in claim 1.

10. An oligonucleotide according to claim 9, having a reporter molecule conjugated thereto.

11. An isolated polynucleotide according to claim 1, which is a 2.9 kilobase EcoRI/EcoRI fragment of plasmid pBS/humEAA4a (ATCC 75245).

12. A recombinant DNA construct having incorporated therein the polynucleotide defined in claim 1.

13. The recombinant DNA construct according to claim 12, wherein said construct is plasmid pBS/humEAA4a (ATCC 75245).

14. A 2.9 kilobase EcoRI/EcoRI fragment of the recombinant DNA construct according to claim 13.

15. A cell that has been engineered genetically to produce a kainate-binding human EAA4 receptor, said cell having incorporated expressibly therein the polynucleotide as recited in claim 1.

16. The cell as defined in claim 15, which is a mammalian cell.

17. The cell as defined in claim 15, which is an oocyte.

18. The membrane preparation derived from the cell as defined in claim 15.

\* \* \* \* \*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2878 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: sig_peptide
        ( B ) LOCATION: 134..226

( i x ) FEATURE:
        ( A ) NAME/KEY: mat_peptide
        ( B ) LOCATION: 227..2860

( i x ) FEATURE:
        ( A ) NAME/KEY: CDS
        ( B ) LOCATION: 134..2860

( x i ) SEQUENCE DESCRIPTION: SEQ ID NO:1:

```
GAATTCCCTC TCTATGACCA TGCCGTGATC GTGTCTGCGG TCACCACTCG ACGCATCCTC          60

ATTTCTACCC GAACCCAGGA GCCGAACGCT AGATCGGGGA AGTGGGTGCC GTGCGTGTGG         120

GCACAGAAAC ACC ATG AAG ATT ATT TTC CCG ATT CTA AGT AAT CCA GTC           169
           Met Lys Ile Ile Phe Pro Ile Leu Ser Asn Pro Val
           -31 -30                    -25                 -20

TTC AGG CGC ACC GTT AAA CTC CTG CTC TGT TTA CTG TGG ATT GGA TAT          217
Phe Arg Arg Thr Val Lys Leu Leu Leu Cys Leu Leu Trp Ile Gly Tyr
             -15                 -10                     -5

TCT CAA GGA ACC ACA CAT GTA TTA AGA TTT GGT GGT ATT TTT GAA TAT          265
Ser Gln Gly Thr Thr His Val Leu Arg Phe Gly Gly Ile Phe Glu Tyr
           1               5                      10

GTG GAA TCT GGC CCA ATG GGA GCT GAG GAA CTT GCA TTC AGA TTT GCT          313
Val Glu Ser Gly Pro Met Gly Ala Glu Glu Leu Ala Phe Arg Phe Ala
        15              20                  25
```

-continued

| | | | | | | | | | | | | | | |
|---|---|---|---|---|---|---|---|---|---|---|---|---|---|---|
| GTG | AAC | ACA | ATT | AAC | AGA | AAC | AGA | ACA | TTG | CTA | CCC | AAT | ACT | ACC | CTT | 361 |
| Val | Asn | Thr | Ile | Asn | Arg | Asn | Arg | Thr | Leu | Leu | Pro | Asn | Thr | Thr | Leu | |
| 30 | | | | | 35 | | | | | 40 | | | | | 45 | |
| ACC | TAT | GAT | ACC | CAG | AAG | ATA | AAC | CTT | TAT | GAT | AGT | TTT | GAA | GCA | TCC | 409 |
| Thr | Tyr | Asp | Thr | Gln | Lys | Ile | Asn | Leu | Tyr | Asp | Ser | Phe | Glu | Ala | Ser | |
| | | | | 50 | | | | | 55 | | | | | 60 | | |
| AAG | AAA | GCC | TGT | GAT | CAG | CTG | TCT | CTT | GGG | GTG | GCT | GCC | ATC | TTC | GGG | 457 |
| Lys | Lys | Ala | Cys | Asp | Gln | Leu | Ser | Leu | Gly | Val | Ala | Ala | Ile | Phe | Gly | |
| | | | 65 | | | | | 70 | | | | | 75 | | | |
| CCT | TCA | CAC | AGC | TCA | TCA | GCA | AAC | GCA | GTG | CAG | TCC | ATC | TGC | AAT | GCT | 505 |
| Pro | Ser | His | Ser | Ser | Ser | Ala | Asn | Ala | Val | Gln | Ser | Ile | Cys | Asn | Ala | |
| | | 80 | | | | | 85 | | | | | 90 | | | | |
| CTG | GGA | GTT | CCC | CAC | ATA | CAG | ACC | CGC | TGG | AAG | CAC | CAG | GTG | TCA | GAC | 553 |
| Leu | Gly | Val | Pro | His | Ile | Gln | Thr | Arg | Trp | Lys | His | Gln | Val | Ser | Asp | |
| | 95 | | | | | 100 | | | | | 105 | | | | | |
| AAC | AAA | GAT | TCC | TTC | TAT | GTC | AGT | CTC | TAC | CCA | GAC | TTC | TCT | TCA | CTC | 601 |
| Asn | Lys | Asp | Ser | Phe | Tyr | Val | Ser | Leu | Tyr | Pro | Asp | Phe | Ser | Ser | Leu | |
| 110 | | | | | 115 | | | | | 120 | | | | | 125 | |
| AGC | CGT | GCC | ATT | TTA | GAC | CTG | GTG | CAG | TTT | TTC | AAG | TGG | AAA | ACC | GTC | 649 |
| Ser | Arg | Ala | Ile | Leu | Asp | Leu | Val | Gln | Phe | Phe | Lys | Trp | Lys | Thr | Val | |
| | | | | 130 | | | | | 135 | | | | | 140 | | |
| ACG | GTT | GTG | TAT | GAT | GAC | AGC | ACT | GGT | CTC | ATT | CGT | TTG | CAA | GAG | CTC | 697 |
| Thr | Val | Val | Tyr | Asp | Asp | Ser | Thr | Gly | Leu | Ile | Arg | Leu | Gln | Glu | Leu | |
| | | | 145 | | | | | 150 | | | | | 155 | | | |
| ATC | AAA | GCT | CCA | TCA | AGG | TAT | AAT | CTT | CGA | CTC | AAA | ATT | CGT | CAG | TTA | 745 |
| Ile | Lys | Ala | Pro | Ser | Arg | Tyr | Asn | Leu | Arg | Leu | Lys | Ile | Arg | Gln | Leu | |
| | | 160 | | | | | 165 | | | | | 170 | | | | |
| CCT | GCT | GAT | ACA | AAG | GAT | GCA | AAA | CCC | TTA | CTA | AAA | GAA | ATG | AAA | AGA | 793 |
| Pro | Ala | Asp | Thr | Lys | Asp | Ala | Lys | Pro | Leu | Leu | Lys | Glu | Met | Lys | Arg | |
| | 175 | | | | | 180 | | | | | 185 | | | | | |
| GGC | AAG | GAG | TTT | CAT | GTA | ATC | TTT | GAT | TGT | AGC | CAT | GAA | ATG | GCA | GCA | 841 |
| Gly | Lys | Glu | Phe | His | Val | Ile | Phe | Asp | Cys | Ser | His | Glu | Met | Ala | Ala | |
| 190 | | | | | 195 | | | | | 200 | | | | | 205 | |
| GGC | ATT | TTA | AAA | CAG | GCA | TTA | GCT | ATG | GGA | ATG | ATG | ACA | GAA | TAC | TAT | 889 |
| Gly | Ile | Leu | Lys | Gln | Ala | Leu | Ala | Met | Gly | Met | Met | Thr | Glu | Tyr | Tyr | |
| | | | | 210 | | | | | 215 | | | | | 220 | | |
| CAT | TAT | ATC | TTT | ACC | ACT | CTG | GAC | CTC | TTT | GCT | CTT | GAT | GTT | GAG | CCC | 937 |
| His | Tyr | Ile | Phe | Thr | Thr | Leu | Asp | Leu | Phe | Ala | Leu | Asp | Val | Glu | Pro | |
| | | | 225 | | | | | 230 | | | | | 235 | | | |
| TAC | CGA | TAC | AGT | GGT | GTT | AAC | ATG | ACA | GGG | TTC | AGA | ATA | TTA | AAT | ACA | 985 |
| Tyr | Arg | Tyr | Ser | Gly | Val | Asn | Met | Thr | Gly | Phe | Arg | Ile | Leu | Asn | Thr | |
| | | 240 | | | | | 245 | | | | | 250 | | | | |
| GAA | AAT | ACC | CAA | GTC | TCC | TCC | ATC | ATT | GAA | AAG | TGG | TCG | ATG | GAA | CGA | 1033 |
| Glu | Asn | Thr | Gln | Val | Ser | Ser | Ile | Ile | Glu | Lys | Trp | Ser | Met | Glu | Arg | |
| | 255 | | | | | 260 | | | | | 265 | | | | | |
| TTG | CAG | GCA | CCT | CCG | AAA | CCC | GAT | TCA | GGT | TTG | CTG | GAT | GGA | TTT | ATG | 1081 |
| Leu | Gln | Ala | Pro | Pro | Lys | Pro | Asp | Ser | Gly | Leu | Leu | Asp | Gly | Phe | Met | |
| 270 | | | | | 275 | | | | | 280 | | | | | 285 | |
| ACG | ACT | GAT | GCT | GCT | CTA | ATG | TAT | GAT | GCT | GTG | CAT | GTG | GTG | TCT | GTG | 1129 |
| Thr | Thr | Asp | Ala | Ala | Leu | Met | Tyr | Asp | Ala | Val | His | Val | Val | Ser | Val | |
| | | | | 290 | | | | | 295 | | | | | 300 | | |
| GCC | GTT | CAA | CAG | TTT | CCC | CAG | ATG | ACA | GTC | AGT | TCC | TTG | CAG | TGT | AAT | 1177 |
| Ala | Val | Gln | Gln | Phe | Pro | Gln | Met | Thr | Val | Ser | Ser | Leu | Gln | Cys | Asn | |
| | | | 305 | | | | | 310 | | | | | 315 | | | |
| CGA | CAT | AAA | CCC | TGG | CGC | TTC | GGG | ACC | CGC | TTT | ATG | AGT | CTA | ATT | AAA | 1225 |
| Arg | His | Lys | Pro | Trp | Arg | Phe | Gly | Thr | Arg | Phe | Met | Ser | Leu | Ile | Lys | |
| | | 320 | | | | | 325 | | | | | 330 | | | | |
| GAG | GCA | CAT | TGG | GAA | GGC | CTC | ACA | GGC | AGA | ATA | ACT | TTC | AAC | AAA | ACC | 1273 |
| Glu | Ala | His | Trp | Glu | Gly | Leu | Thr | Gly | Arg | Ile | Thr | Phe | Asn | Lys | Thr | |
| | 335 | | | | | 340 | | | | | 345 | | | | | |

```
AAT GGC TTG AGA ACA GAT TTT GAT TTG GAT GTG ATC AGT CTG AAG GAA      1321
Asn Gly Leu Arg Thr Asp Phe Asp Leu Asp Val Ile Ser Leu Lys Glu
350             355             360             365

GAA GGT CTA GAA AAG ATT GGA ACG TGG GAT CCA GCC AGT GGC CTG AAT      1369
Glu Gly Leu Glu Lys Ile Gly Thr Trp Asp Pro Ala Ser Gly Leu Asn
                370             375             380

ATG ACA GAA AGT CAA AAG GGA AAG CCA GCG AAC ATC ACA GAT TCC TTA      1417
Met Thr Glu Ser Gln Lys Gly Lys Pro Ala Asn Ile Thr Asp Ser Leu
            385             390             395

TCC AAT CGT TCT TTG ATT GTT ACC ACC ATT TTG GAA GAG CCT TAT GTC      1465
Ser Asn Arg Ser Leu Ile Val Thr Thr Ile Leu Glu Glu Pro Tyr Val
        400             405             410

CTT TTT AAG AAG TCT GAC AAA CCT CTC TAT GGT AAT GAT CGA TTT GAA      1513
Leu Phe Lys Lys Ser Asp Lys Pro Leu Tyr Gly Asn Asp Arg Phe Glu
    415             420             425

GGC TAT TGC ATT GAT CTC CTC AGA GAG TTA TCT ACA ATC CTT GGC TTT      1561
Gly Tyr Cys Ile Asp Leu Leu Arg Glu Leu Ser Thr Ile Leu Gly Phe
430             435             440             445

ACA TAT GAA ATT AGA CTT GTG GAA GAT GGG AAA TAT GGA GCC CAG GAT      1609
Thr Tyr Glu Ile Arg Leu Val Glu Asp Gly Lys Tyr Gly Ala Gln Asp
            450             455             460

GAT GCC AAT GGA CAA TGG AAT GGA ATG GTT CGT GAA CTA ATT GAT CAT      1657
Asp Ala Asn Gly Gln Trp Asn Gly Met Val Arg Glu Leu Ile Asp His
        465             470             475

AAA GCT GAC CTT GCA GTT GCT CCA CTG GCT ATT ACC TAT GTT CGA GAG      1705
Lys Ala Asp Leu Ala Val Ala Pro Leu Ala Ile Thr Tyr Val Arg Glu
    480             485             490

AAG GTC ATC GAC TTT TCC AAG CCC TTT ATG ACA CTT GGA ATA AGT ATT      1753
Lys Val Ile Asp Phe Ser Lys Pro Phe Met Thr Leu Gly Ile Ser Ile
495             500             505

TTG TAC CGC AAG CCC AAT GGT ACA AAC CCA GGC GTC TTC TCC TTC CTG      1801
Leu Tyr Arg Lys Pro Asn Gly Thr Asn Pro Gly Val Phe Ser Phe Leu
510             515             520             525

AAT CCT CTC TCC CCT GAT ATC TGG ATG TAT ATT CTG CTG GCT TAC TTG      1849
Asn Pro Leu Ser Pro Asp Ile Trp Met Tyr Ile Leu Leu Ala Tyr Leu
            530             535             540

GGT GTC AGT TGT GTG CTC TTT GTC ATA GCC AGG TTT AGT CCT TAT GAG      1897
Gly Val Ser Cys Val Leu Phe Val Ile Ala Arg Phe Ser Pro Tyr Glu
        545             550             555

TGG TAT AAT CCA CAC CCT TGC AAC CCT GAC TCA GAC GTG GTG GAA AAC      1945
Trp Tyr Asn Pro His Pro Cys Asn Pro Asp Ser Asp Val Val Glu Asn
    560             565             570

AAT TTT ACC TTG CTA AAT AGT TTC TGG TTT GGA GTT GGA GCT CTC ATG      1993
Asn Phe Thr Leu Leu Asn Ser Phe Trp Phe Gly Val Gly Ala Leu Met
575             580             585

CAG CAA GGT TCT GAG CTC ATG CCC AAA GCA CTG TCC ACC AGG ATA GTG      2041
Gln Gln Gly Ser Glu Leu Met Pro Lys Ala Leu Ser Thr Arg Ile Val
590             595             600             605

GGA GGC ATT TGG TGG TTT TTC ACA CTT ATC ATC ATT TCT TCG TAT ACT      2089
Gly Gly Ile Trp Trp Phe Phe Thr Leu Ile Ile Ile Ser Ser Tyr Thr
            610             615             620

GCT AAC TTA GCC GCC TTT CTG ACA GTG GAA CGC ATG GAA TCC CCT ATT      2137
Ala Asn Leu Ala Ala Phe Leu Thr Val Glu Arg Met Glu Ser Pro Ile
        625             630             635

GAC TCT GCT GAT GAT TTA GCT AAA CAA ACC AAG ATA GAA TAT GGA GCA      2185
Asp Ser Ala Asp Asp Leu Ala Lys Gln Thr Lys Ile Glu Tyr Gly Ala
    640             645             650

GTA GAG GAT GGT GCA ACC ATG ACT TTT TTC AAG AAA TCA AAA ATC TCC      2233
Val Glu Asp Gly Ala Thr Met Thr Phe Phe Lys Lys Ser Lys Ile Ser
655             660             665
```

| | | | | | | | | | | | | | | | | |
|---|---|---|---|---|---|---|---|---|---|---|---|---|---|---|---|---|
| ACG | TAT | GAC | AAA | ATG | TGG | GCC | TTT | ATG | AGT | AGC | AGA | AGG | CAG | TCA | GTG | 2281 |
| Thr | Tyr | Asp | Lys | Met | Trp | Ala | Phe | Met | Ser | Ser | Arg | Arg | Gln | Ser | Val | |
| 670 | | | | 675 | | | | | 680 | | | | | 685 | | |
| CTG | GTC | AAA | AGT | AAT | GAA | GAA | GGA | ATC | CAG | CGA | GTC | CTC | ACC | TCT | GAT | 2329 |
| Leu | Val | Lys | Ser | Asn | Glu | Glu | Gly | Ile | Gln | Arg | Val | Leu | Thr | Ser | Asp | |
| | | | | 690 | | | | | 695 | | | | | 700 | | |
| TAT | GCT | TTC | CTA | ATG | GAG | TCA | ACA | ACC | ATC | GAG | TTT | GTT | ACC | CAG | CGG | 2377 |
| Tyr | Ala | Phe | Leu | Met | Glu | Ser | Thr | Thr | Ile | Glu | Phe | Val | Thr | Gln | Arg | |
| | | | 705 | | | | | 710 | | | | | 715 | | | |
| AAC | TGT | AAC | CTG | ACA | CAG | ATT | GGC | GGC | CTT | ATA | GAC | TCT | AAA | GGT | TAT | 2425 |
| Asn | Cys | Asn | Leu | Thr | Gln | Ile | Gly | Gly | Leu | Ile | Asp | Ser | Lys | Gly | Tyr | |
| | | 720 | | | | | 725 | | | | | 730 | | | | |
| GGC | GTT | GGC | ACT | CCC | ATG | GGT | TCT | CCA | TAT | CGA | GAC | AAA | ATT | ACC | ATA | 2473 |
| Gly | Val | Gly | Thr | Pro | Met | Gly | Ser | Pro | Tyr | Arg | Asp | Lys | Ile | Thr | Ile | |
| | | 735 | | | | | 740 | | | | | 745 | | | | |
| GCA | ATT | CTT | CAG | CTG | CAA | GAG | GAA | GGC | AAA | CTG | CAT | ATG | ATG | AAG | GAG | 2521 |
| Ala | Ile | Leu | Gln | Leu | Gln | Glu | Glu | Gly | Lys | Leu | His | Met | Met | Lys | Glu | |
| 750 | | | | | 755 | | | | | 760 | | | | | 765 | |
| AAA | TGG | TGG | AGG | GGC | AAT | GGT | TGC | CCA | GAA | GAG | GAA | AGC | AAA | GAG | GCC | 2569 |
| Lys | Trp | Trp | Arg | Gly | Asn | Gly | Cys | Pro | Glu | Glu | Glu | Ser | Lys | Glu | Ala | |
| | | | | 770 | | | | | 775 | | | | | 780 | | |
| AGT | GCC | CTG | GGG | GTT | CAG | AAT | ATT | GGT | GGC | ATC | TTC | ATT | GTT | CTG | GCA | 2617 |
| Ser | Ala | Leu | Gly | Val | Gln | Asn | Ile | Gly | Gly | Ile | Phe | Ile | Val | Leu | Ala | |
| | | | 785 | | | | | 790 | | | | | 795 | | | |
| GCC | GGC | TTG | GTG | CTT | TCA | GTT | TTT | GTG | GCA | GTG | GGA | GAA | TTT | TTA | TAC | 2665 |
| Ala | Gly | Leu | Val | Leu | Ser | Val | Phe | Val | Ala | Val | Gly | Glu | Phe | Leu | Tyr | |
| | | | 800 | | | | | 805 | | | | | 810 | | | |
| AAA | TCC | AAA | AAA | AAC | GCT | CAA | TTG | GAA | AAG | AGG | TCC | TTC | TGT | AGT | GCC | 2713 |
| Lys | Ser | Lys | Lys | Asn | Ala | Gln | Leu | Glu | Lys | Arg | Ser | Phe | Cys | Ser | Ala | |
| | | 815 | | | | | 820 | | | | | 825 | | | | |
| ATG | GTA | GAA | GAA | TTG | AGG | ATG | TCC | CTG | AAG | TGC | CAG | CGT | CGG | TTA | AAA | 2761 |
| Met | Val | Glu | Glu | Leu | Arg | Met | Ser | Leu | Lys | Cys | Gln | Arg | Arg | Leu | Lys | |
| 830 | | | | | 835 | | | | | 840 | | | | | 845 | |
| CAT | AAG | CCA | CAG | GCC | CCA | GTT | ATT | GTG | AAA | ACA | GAA | GAA | GTT | ATC | AAC | 2809 |
| His | Lys | Pro | Gln | Ala | Pro | Val | Ile | Val | Lys | Thr | Glu | Glu | Val | Ile | Asn | |
| | | | | 850 | | | | | 855 | | | | | 860 | | |
| ATG | CAC | ACA | TTT | AAC | GAC | AGA | AGG | TTG | CCA | GGT | AAA | GAA | ACC | ATG | GCA | 2857 |
| Met | His | Thr | Phe | Asn | Asp | Arg | Arg | Leu | Pro | Gly | Lys | Glu | Thr | Met | Ala | |
| | | | 865 | | | | | 870 | | | | | 875 | | | |

TAAAGCTGGG AGGCGGAATT C    2878

( 2 ) INFORMATION FOR SEQ ID NO:2:

( i ) SEQUENCE CHARACTERISTICS:
        ( A ) LENGTH: 908 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Ile | Ile | Phe | Pro | Ile | Leu | Ser | Asn | Pro | Val | Phe | Arg | Arg | Thr |
| -31 | -30 | | | | | -25 | | | | | -20 | | | | |
| Val | Lys | Leu | Leu | Leu | Cys | Leu | Leu | Trp | Ile | Gly | Tyr | Ser | Gln | Gly | Thr |
| -15 | | | | | -10 | | | | | -5 | | | | | 1 |
| Thr | His | Val | Leu | Arg | Phe | Gly | Gly | Ile | Phe | Glu | Tyr | Val | Glu | Ser | Gly |
| | | | | 5 | | | | | 10 | | | | | 15 | |
| Pro | Met | Gly | Ala | Glu | Glu | Leu | Ala | Phe | Arg | Phe | Ala | Val | Asn | Thr | Ile |
| | | | 20 | | | | | 25 | | | | | 30 | | |
| Asn | Arg | Asn | Arg | Thr | Leu | Leu | Pro | Asn | Thr | Thr | Leu | Thr | Tyr | Asp | Thr |

-continued

|  | 35 |  |  |  | 40 |  |  |  | 45 |  |  |  |
|---|---|---|---|---|---|---|---|---|---|---|---|---|
| Gln | Lys | Ile | Asn | Leu | Tyr | Asp | Ser | Phe | Glu | Ala | Ser | Lys | Lys | Ala | Cys |
| 50 |  |  |  | 55 |  |  |  | 60 |  |  |  | 65 |
| Asp | Gln | Leu | Ser | Leu | Gly | Val | Ala | Ala | Ile | Phe | Gly | Pro | Ser | His | Ser |
|  |  |  |  | 70 |  |  |  | 75 |  |  |  | 80 |  |
| Ser | Ser | Ala | Asn | Ala | Val | Gln | Ser | Ile | Cys | Asn | Ala | Leu | Gly | Val | Pro |
|  |  |  | 85 |  |  |  |  | 90 |  |  |  |  | 95 |  |  |
| His | Ile | Gln | Thr | Arg | Trp | Lys | His | Gln | Val | Ser | Asp | Asn | Lys | Asp | Ser |
|  |  | 100 |  |  |  |  | 105 |  |  |  |  | 110 |  |  |  |
| Phe | Tyr | Val | Ser | Leu | Tyr | Pro | Asp | Phe | Ser | Ser | Leu | Ser | Arg | Ala | Ile |
|  | 115 |  |  |  | 120 |  |  |  |  | 125 |  |  |  |  |  |
| Leu | Asp | Leu | Val | Gln | Phe | Lys | Trp | Lys | Thr | Val | Thr | Val | Val | Tyr |
| 130 |  |  |  | 135 |  |  |  | 140 |  |  |  | 145 |
| Asp | Asp | Ser | Thr | Gly | Leu | Ile | Arg | Leu | Gln | Glu | Leu | Ile | Lys | Ala | Pro |
|  |  |  |  | 150 |  |  |  |  | 155 |  |  |  |  | 160 |  |
| Ser | Arg | Tyr | Asn | Leu | Arg | Leu | Lys | Ile | Arg | Gln | Leu | Pro | Ala | Asp | Thr |
|  |  |  | 165 |  |  |  |  | 170 |  |  |  | 175 |  |  |  |
| Lys | Asp | Ala | Lys | Pro | Leu | Leu | Lys | Glu | Met | Lys | Arg | Gly | Lys | Glu | Phe |
|  |  | 180 |  |  |  |  | 185 |  |  |  |  | 190 |  |  |  |
| His | Val | Ile | Phe | Asp | Cys | Ser | His | Glu | Met | Ala | Ala | Gly | Ile | Leu | Lys |
|  | 195 |  |  |  | 200 |  |  |  |  | 205 |  |  |  |  |  |
| Gln | Ala | Leu | Ala | Met | Gly | Met | Met | Thr | Glu | Tyr | Tyr | His | Tyr | Ile | Phe |
| 210 |  |  |  | 215 |  |  |  | 220 |  |  |  | 225 |
| Thr | Thr | Leu | Asp | Leu | Phe | Ala | Leu | Asp | Val | Glu | Pro | Tyr | Arg | Tyr | Ser |
|  |  |  |  | 230 |  |  |  |  | 235 |  |  |  | 240 |  |  |
| Gly | Val | Asn | Met | Thr | Gly | Phe | Arg | Ile | Leu | Asn | Thr | Glu | Asn | Thr | Gln |
|  |  |  | 245 |  |  |  |  | 250 |  |  |  |  | 255 |  |  |
| Val | Ser | Ser | Ile | Ile | Glu | Lys | Trp | Ser | Met | Glu | Arg | Leu | Gln | Ala | Pro |
|  |  | 260 |  |  |  |  | 265 |  |  |  |  | 270 |  |  |  |
| Pro | Lys | Pro | Asp | Ser | Gly | Leu | Leu | Asp | Gly | Phe | Met | Thr | Thr | Asp | Ala |
|  | 275 |  |  |  | 280 |  |  |  |  | 285 |  |  |  |  |  |
| Ala | Leu | Met | Tyr | Asp | Ala | Val | His | Val | Val | Ser | Val | Ala | Val | Gln | Gln |
| 290 |  |  |  | 295 |  |  |  | 300 |  |  |  | 305 |
| Phe | Pro | Gln | Met | Thr | Val | Ser | Ser | Leu | Gln | Cys | Asn | Arg | His | Lys | Pro |
|  |  |  |  | 310 |  |  |  |  | 315 |  |  |  | 320 |  |  |
| Trp | Arg | Phe | Gly | Thr | Arg | Phe | Met | Ser | Leu | Ile | Lys | Glu | Ala | His | Trp |
|  |  |  | 325 |  |  |  |  | 330 |  |  |  |  | 335 |  |  |
| Glu | Gly | Leu | Thr | Gly | Arg | Ile | Thr | Phe | Asn | Lys | Thr | Asn | Gly | Leu | Arg |
|  |  | 340 |  |  |  |  | 345 |  |  |  |  | 350 |  |  |  |
| Thr | Asp | Phe | Asp | Leu | Asp | Val | Ile | Ser | Leu | Lys | Glu | Glu | Gly | Leu | Glu |
|  | 355 |  |  |  | 360 |  |  |  |  | 365 |  |  |  |  |  |
| Lys | Ile | Gly | Thr | Trp | Asp | Pro | Ala | Ser | Gly | Leu | Asn | Met | Thr | Glu | Ser |
| 370 |  |  |  | 375 |  |  |  | 380 |  |  |  | 385 |
| Gln | Lys | Gly | Lys | Pro | Ala | Asn | Ile | Thr | Asp | Ser | Leu | Ser | Asn | Arg | Ser |
|  |  |  |  | 390 |  |  |  | 395 |  |  |  | 400 |  |  |
| Leu | Ile | Val | Thr | Thr | Ile | Leu | Glu | Glu | Pro | Tyr | Val | Leu | Phe | Lys | Lys |
|  |  |  | 405 |  |  |  |  | 410 |  |  |  |  | 415 |  |  |
| Ser | Asp | Lys | Pro | Leu | Tyr | Gly | Asn | Asp | Arg | Phe | Glu | Gly | Tyr | Cys | Ile |
|  |  | 420 |  |  |  |  | 425 |  |  |  |  | 430 |  |  |  |
| Asp | Leu | Leu | Arg | Glu | Leu | Ser | Thr | Ile | Leu | Gly | Phe | Thr | Tyr | Glu | Ile |
|  |  | 435 |  |  |  |  | 440 |  |  |  |  | 445 |  |  |  |
| Arg | Leu | Val | Glu | Asp | Gly | Lys | Tyr | Gly | Ala | Gln | Asp | Asp | Ala | Asn | Gly |
| 450 |  |  |  | 455 |  |  |  | 460 |  |  |  | 465 |

Gln Trp Asn Gly Met Val Arg Glu Leu Ile Asp His Lys Ala Asp Leu
                        470                 475                 480

Ala Val Ala Pro Leu Ala Ile Thr Tyr Val Arg Glu Lys Val Ile Asp
            485                 490                 495

Phe Ser Lys Pro Phe Met Thr Leu Gly Ile Ser Ile Leu Tyr Arg Lys
            500                 505                 510

Pro Asn Gly Thr Asn Pro Gly Val Phe Ser Phe Leu Asn Pro Leu Ser
            515                 520                 525

Pro Asp Ile Trp Met Tyr Ile Leu Leu Ala Tyr Leu Gly Val Ser Cys
530                     535                 540                 545

Val Leu Phe Val Ile Ala Arg Phe Ser Pro Tyr Glu Trp Tyr Asn Pro
                550                 555                 560

His Pro Cys Asn Pro Asp Ser Asp Val Val Glu Asn Asn Phe Thr Leu
            565                 570                 575

Leu Asn Ser Phe Trp Phe Gly Val Gly Ala Leu Met Gln Gln Gly Ser
            580                 585                 590

Glu Leu Met Pro Lys Ala Leu Ser Thr Arg Ile Val Gly Gly Ile Trp
        595                 600                 605

Trp Phe Phe Thr Leu Ile Ile Ile Ser Ser Tyr Thr Ala Asn Leu Ala
610                     615                 620                 625

Ala Phe Leu Thr Val Glu Arg Met Glu Ser Pro Ile Asp Ser Ala Asp
                630                 635                 640

Asp Leu Ala Lys Gln Thr Lys Ile Glu Tyr Gly Ala Val Glu Asp Gly
            645                 650                 655

Ala Thr Met Thr Phe Phe Lys Lys Ser Lys Ile Ser Thr Tyr Asp Lys
            660                 665                 670

Met Trp Ala Phe Met Ser Ser Arg Arg Gln Ser Val Leu Val Lys Ser
    675                 680                 685

Asn Glu Glu Gly Ile Gln Arg Val Leu Thr Ser Asp Tyr Ala Phe Leu
690                 695                 700                 705

Met Glu Ser Thr Thr Ile Glu Phe Val Thr Gln Arg Asn Cys Asn Leu
                710                 715                 720

Thr Gln Ile Gly Gly Leu Ile Asp Ser Lys Gly Tyr Gly Val Gly Thr
            725                 730                 735

Pro Met Gly Ser Pro Tyr Arg Asp Lys Ile Thr Ile Ala Ile Leu Gln
        740                 745                 750

Leu Gln Glu Glu Gly Lys Leu His Met Met Lys Glu Lys Trp Trp Arg
    755                 760                 765

Gly Asn Gly Cys Pro Glu Glu Glu Ser Lys Glu Ala Ser Ala Leu Gly
770                 775                 780                 785

Val Gln Asn Ile Gly Gly Ile Phe Ile Val Leu Ala Ala Gly Leu Val
            790                 795                 800

Leu Ser Val Phe Val Ala Val Gly Glu Phe Leu Tyr Lys Ser Lys Lys
            805                 810                 815

Asn Ala Gln Leu Glu Lys Arg Ser Phe Cys Ser Ala Met Val Glu Glu
        820                 825                 830

Leu Arg Met Ser Leu Lys Cys Gln Arg Arg Leu Lys His Lys Pro Gln
    835                 840                 845

Ala Pro Val Ile Val Lys Thr Glu Glu Val Ile Asn Met His Thr Phe
850                 855                 860                 865

Asn Asp Arg Arg Leu Pro Gly Lys Glu Thr Met Ala
            870                 875

( 2 ) INFORMATION FOR SEQ ID NO:3:

( i ) SEQUENCE CHARACTERISTICS:
    ( A ) LENGTH: 50 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:3:

GGAACTGTAA CCTGACACAG ATTGGCGGCC TTATAGACTC TAAAGGTTAT    50

( 2 ) INFORMATION FOR SEQ ID NO:4:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

GGAACTGTAA CCTGACACAG ATTGGCGACC TTATAGACTC TAAAGGTTAT    50

( 2 ) INFORMATION FOR SEQ ID NO:5:

( i ) SEQUENCE CHARACTERISTICS:
        ( A ) LENGTH: 50 amino acids
        ( B ) TYPE: amino acid
        ( D ) TOPOLOGY: linear ( x i ) SEQUENCE DESCRIPTION: SEQ ID NO:5:

```
Ser  Asp  Tyr  Ala  Phe  Leu  Met  Glu  Ser  Thr  Thr  Ile  Glu  Phe  Val  Thr
 1              5                        10                       15

Gln  Arg  Asn  Cys  Asn  Leu  Thr  Gln  Ile  Gly  Gly  Leu  Ile  Asp  Ser  Lys
               20                        25                      30

Gly  Tyr  Gly  Val  Gly  Thr  Pro  Met  Gly  Ser  Pro  Tyr  Arg  Asp  Lys  Ile
               35                        40                      45

Thr  Ile
     50
```

( 2 ) INFORMATION FOR SEQ ID NO:6:

( i ) SEQUENCE CHARACTERISTICS:
        ( A ) LENGTH: 50 amino acids
        ( B ) TYPE: amino acid
        ( D ) TOPOLOGY: linear ( x i ) SEQUENCE DESCRIPTION: SEQ ID NO:6:

```
Ser  Asp  Tyr  Ala  Phe  Leu  Met  Glu  Ser  Thr  Thr  Ile  Glu  Phe  Val  Thr
 1              5                        10                       15

Gln  Arg  Asn  Cys  Asn  Leu  Thr  Gln  Ile  Gly  Asp  Leu  Ile  Asp  Ser  Lys
               20                        25                      30

Gly  Tyr  Gly  Val  Gly  Thr  Pro  Met  Gly  Ser  Pro  Tyr  Arg  Asp  Lys  Ile
               35                        40                      45

Thr  Ile
     50
```

( 2 ) INFORMATION FOR SEQ ID NO:7:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:7:

GGTTTGGAGT TGGAGCTCTC ATGCAGCAAG GTTCTGAGCT CATGCCCAAA    50

(2) INFORMATION FOR SEQ ID NO:8:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (xi) SEQUENCE DESCRIPTION: SEQ ID NO:8:

```
GGTTTGGAGT TGGAGCTCTC ATGCAACAAG GTTCTGAGCT CATGCCCAAA        50
```

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:9:

```
ATCGGCGGCA TCTTCATTGT TCTGGCTGCA GGACTCGTGC        40
```